(12) United States Patent
Wakimoto et al.

(10) Patent No.: US 9,970,371 B2
(45) Date of Patent: *May 15, 2018

(54) CONTROL APPARATUS AND CONTROL METHOD FOR INTERNAL COMBUSTION ENGINE

(71) Applicant: TOYOTA JIDOSHA KABUSHIKI KAISHA, Toyota-shi, Aichi-ken (JP)

(72) Inventors: Michihiro Wakimoto, Okazaki (JP); Keigo Mizutani, Okazaki (JP); Tatsuhiro Hashida, Shizuoka-ken (JP); Kazuhiro Wakao, Susono (JP); Keiichiro Aoki, Shizuoka-ken (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 106 days.

This patent is subject to a terminal disclaimer.

(21) Appl. No.: 14/912,786

(22) PCT Filed: Aug. 13, 2014

(86) PCT No.: PCT/IB2014/001511
§ 371 (c)(1),
(2) Date: Feb. 18, 2016

(87) PCT Pub. No.: WO2015/025202
PCT Pub. Date: Feb. 26, 2015

(65) Prior Publication Data
US 2016/0208721 A1 Jul. 21, 2016

(30) Foreign Application Priority Data
Aug. 23, 2013 (JP) ................. 2013-173210

(51) Int. Cl.
F02D 41/02 (2006.01)
F02D 41/14 (2006.01)
(Continued)

(52) U.S. Cl.
CPC ..... *F02D 41/0295* (2013.01); *F02D 41/1444* (2013.01); *F02D 41/1456* (2013.01);
(Continued)

(58) Field of Classification Search
CPC .................................................. F02D 41/0295
(Continued)

(56) References Cited

U.S. PATENT DOCUMENTS 5,145,566 A   9/1992 Logothetis et al.
6,051,123 A   4/2000 Joshi et al.
(Continued)

FOREIGN PATENT DOCUMENTS

EP   0361692 A2    4/1990
JP   H02-122255 A  5/1990
(Continued)

OTHER PUBLICATIONS

US Patent and Trademark Office, Notice of Allowance in U.S. Appl. No. 14/894,848, dated Sep. 18, 2017, 16 pages.

*Primary Examiner* — John Fitzgerald
*Assistant Examiner* — Jean Morello
(74) *Attorney, Agent, or Firm* — Hunton Andrews Kurth LLP

(57) ABSTRACT

A control apparatus for an internal combustion engine having a limiting current sensor includes an electronic control unit. The electronic control unit is configured to: (i) calculate a parameter relating to SOx contained in a detection subject gas using an output current of the sensor obtained when voltage reduction control is implemented to reduce an applied voltage applied to the sensor from a parameter calculation voltage; and (ii) implement the voltage reduction control when an oxygen concentration of the detection subject gas is less than a predetermined concentration or a low oxygen concentration condition, according to which an oxygen concentration of the detection subject gas is predicted to be less than a predetermined concentration, is established.

15 Claims, 24 Drawing Sheets

(51) Int. Cl.
  *G01N 27/407*  (2006.01)
  *G01N 33/00*  (2006.01)
  *F02D 41/40*  (2006.01)
  *F02D 41/00*  (2006.01)

(52) U.S. Cl.
  CPC ..... *F02D 41/1473* (2013.01); *G01N 27/4074* (2013.01); *G01N 33/0042* (2013.01); *F02D 41/0047* (2013.01); *F02D 41/405* (2013.01)

(58) Field of Classification Search
  USPC ..................................................... 73/114.71
  See application file for complete search history.

(56) References Cited

U.S. PATENT DOCUMENTS

| | | | |
|---|---|---|---|
| 8,707,677 B2* | 4/2014 | Kowalkowski | F02D 41/146 |
| | | | 60/273 |
| 2002/0157379 A1* | 10/2002 | Kakuyama | B01D 53/9454 |
| | | | 60/276 |
| 2002/0173919 A1 | 11/2002 | Moteki et al. | |
| 2005/0040041 A1* | 2/2005 | Sakayanagi | G01N 27/419 |
| | | | 204/427 |
| 2014/0116031 A1 | 5/2014 | Yoshida et al. | |
| 2016/0349206 A1 | 12/2016 | Hashida et al. | |

FOREIGN PATENT DOCUMENTS

| | | |
|---|---|---|
| JP | H03-100454 A | 4/1991 |
| JP | 2002-349250 A | 12/2002 |
| JP | 2008-076410 A | 4/2008 |
| JP | 2015-017931 A | 1/2015 |
| JP | 2015-017932 A | 1/2015 |
| JP | 2015-036538 A | 2/2015 |
| JP | 2015-040546 A | 3/2015 |
| JP | 2015-155665 A | 8/2015 |
| WO | 2013-021703 A1 | 2/2013 |
| WO | 2015/022568 A1 | 2/2015 |
| WO | 2015/025202 A1 | 2/2015 |

* cited by examiner

F I G . 26
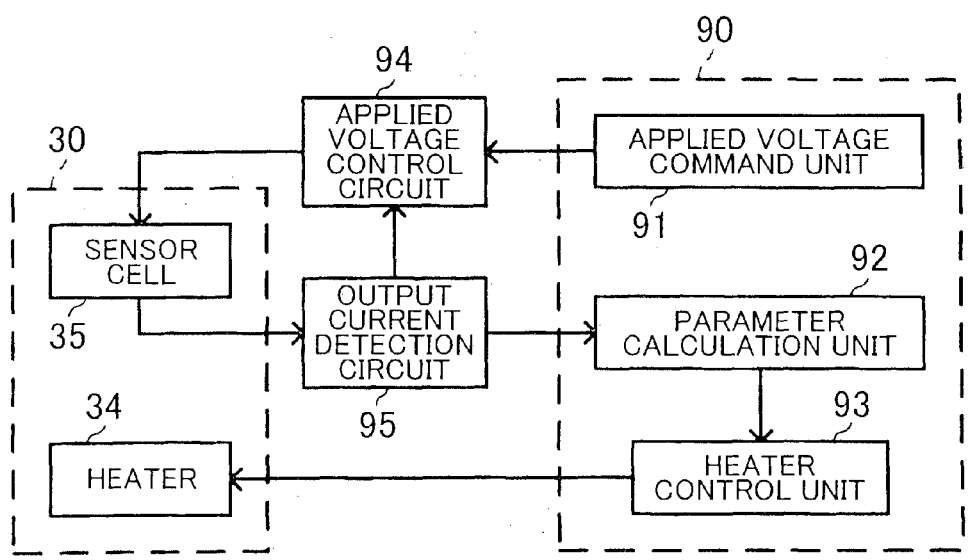

CONTROL APPARATUS AND CONTROL METHOD FOR INTERNAL COMBUSTION ENGINE

CROSS-REFERENCE TO RELATED APPLICATIONS

This is a national phase application based on the PCT International Patent Application No. PCT/IB2014/001511 filed Aug. 13, 2014, claiming priority to Japanese Patent Application No. 2013-173210 filed Aug. 23, 2013, the entire contents of both of which are incorporated herein by reference.

BACKGROUND OF THE INVENTION

1. Field of the Invention

The invention relates to a control apparatus and a control method for an internal combustion engine.

2. Description of Related Art

Japanese Patent Application Publication No. 2-122255 (JP 2-122255 A) describes a method and a device for measuring, in a gas containing two types of oxygen-containing gases, a relative amount of one of the oxygen-containing gases. In JP 2-122255 A, the oxygen-containing gas (water vapor or carbon dioxide, for example) in the gas is measured by controlling a voltage applied to a cell.

In the field of internal combustion engines, it may be necessary to detect a concentration of sulfur oxide (SOx) in exhaust gas. It may be necessary to detect the SOx concentration of the exhaust gas more widely. Even more widely, it may be necessary to calculate a parameter (a "SOx related parameter" hereafter) relating to the SOx in the exhaust gas. The SOx related parameter is preferably calculated with a high degree of precision.

SUMMARY OF THE INVENTION

The invention provides a control apparatus and a control method for an internal combustion engine, with which a parameter relating to SOx in exhaust gas is calculated with a high degree of precision.

A first aspect of the invention is a control apparatus for an internal combustion engine having a limiting current sensor, which includes an electronic control unit. The electronic control unit is configured to: (i) calculate a parameter relating to SOx contained in a detection subject gas using an output current of the sensor obtained when voltage reduction control is implemented to reduce an applied voltage applied to the sensor from a parameter calculation voltage; and (ii) implement the voltage reduction control when an oxygen concentration of the detection subject gas is less than a predetermined concentration.

A second aspect of the invention is a control apparatus for an internal combustion engine having a limiting current sensor, which includes an electronic control unit. The electronic control unit is configured to: (i) calculate a parameter relating to SOx contained in a detection subject gas using an output current of the sensor obtained when voltage reduction control is implemented to reduce an applied voltage applied to the sensor from a parameter calculation voltage; and (ii) implement the voltage reduction control when a low oxygen concentration condition, according to which an oxygen concentration of the detection subject gas is predicted to be less than a predetermined concentration, is established.

According to the configurations described above, the oxygen concentration of the detection subject gas during the voltage reduction control is low. When the oxygen concentration of the detection subject gas during the voltage reduction control is low, a small proportion of the output current obtained during the voltage reduction control is occupied by an output current generated as a result of the oxygen concentration of the detection subject gas. Accordingly, a large proportion of a value of the output current obtained during the voltage reduction control is occupied by an output current generated as a result of the amount of SOx in the detection subject gas. In other words, the output current obtained during the voltage reduction control corresponds to the amount of SOx. Therefore, the SOx related parameter can be calculated with a high degree of precision.

The oxygen concentration may include not only the oxygen concentration of the detection subject gas itself, but also a parameter that correlates with the oxygen concentration of the detection subject gas and a parameter that substantially expresses the oxygen concentration of the detection subject gas.

The low oxygen concentration condition is established when, for example, an exhaust gas recirculation (EGR) rate equals or exceeds a predetermined EGR rate, an EGR valve opening equals or exceeds a predetermined opening, an engine operating condition satisfies a high EGR operation condition, a post injection is implemented, the engine operating condition satisfies a post injection condition, exhaust addition is implemented, or the engine operating condition satisfies an exhaust addition condition.

When the engine operating condition satisfies the high EGR operation condition, the internal combustion engine is operated while controlling the EGR rate to or above the predetermined EGR rate. When the engine operating condition satisfies the post injection condition, the internal combustion engine is operated while implementing a post injection. When the engine operating condition satisfies an exhaust addition condition, the internal combustion engine is operated while implementing exhaust addition.

In the control apparatus described above, the electronic control unit may be configured to implement the voltage reduction control after controlling the oxygen concentration of the detection subject gas at or below the predetermined concentration or after establishing the low oxygen concentration condition. According to this configuration, the oxygen concentration of the detection subject gas is actively controlled at or below the predetermined concentration, and therefore calculation of the SOx related parameter can be implemented at an appropriate timing.

In the control apparatus described above, the electronic control unit may be configured to implement voltage increase control to increase the applied voltage applied to the sensor to the parameter calculation voltage before implementing the voltage reduction control, and control the oxygen concentration of the detection subject gas at or below the predetermined concentration, or establish the low oxygen concentration condition, only during implementation of the voltage reduction control. The output current resulting from the SOx is output during the voltage reduction control rather than the voltage increase control. Hence, by controlling the oxygen concentration of the detection subject gas at or below the predetermined concentration or establishing the low oxygen concentration condition only during implementation of the voltage reduction control, the SOx related parameter can be calculated with a high degree of precision by adding a minimum required amount of control.

In the control apparatus described above, the electronic control unit may be configured to warn that a fuel property is abnormal when an absolute value of the output current during the voltage reduction control equals or exceeds a warning determination value. According to this configuration, when the possibility of an abnormality in the fuel property exists, notification can be provided of the possibility of an abnormality in the fuel property. In this case, definitive calculation of the SOx related parameter is not always necessary. It may be said in this case that a parameter for determining the need to issue a warning indicating an abnormality in the fuel property is calculated as the SOx related parameter.

In the control apparatus described above, the electronic control unit may be configured to implement voltage increase control to increase the applied voltage applied to the sensor to the parameter calculation voltage before implementing the voltage reduction control and when a temperature of the sensor is less than a predetermined upper limit temperature. According to this configuration, the sensor temperature during the voltage increase control is low. When the sensor temperature during the voltage increase control is low, SOx (in particular, a sulfur component) that adheres to the sensor during the voltage increase control is less likely to separate from the sensor (or at least separation of the SOx adhered to the sensor from the sensor is suppressed), and therefore the output current of the sensor during the voltage reduction control implemented after the voltage increase control corresponds to the amount of SOx. As a result, the SOx related parameter can be calculated with an even higher degree of precision.

In the control apparatus described above, the electronic control unit may be configured to employ a parameter calculated when the oxygen concentration of the detection subject gas is lowest, from among a plurality of calculated parameters, as a final parameter relating to SOx. The output current obtained during the voltage reduction control corresponds steadily more closely to the amount of SOx as the oxygen concentration of the exhaust gas decreases. Therefore, by employing a SOx related parameter calculated when the oxygen concentration of the detection subject gas is low as the final SOx related parameter, the SOx related parameter can be calculated with an even higher degree of precision. This concept is particularly useful in a case where the oxygen concentration of the detection subject gas during the voltage reduction control differs in each implementation of the voltage reduction control. In other words, this concept is particularly useful in a case where the voltage reduction control is implemented when the oxygen concentration of the detection subject gas falls at or below the predetermined concentration, rather than after actively controlling the oxygen concentration of the detection subject gas at or below the predetermined concentration.

The SOx related parameter is, for example, the SOx concentration, or a coefficient that is used to control the internal combustion engine and set in accordance with the SOx concentration.

In the control apparatus described above, the electronic control unit may be configured to implement control to eliminate sulfur poisoning from the sensor when the output current during the voltage reduction control equals or exceeds a determination value. According to this configuration, in a case where sulfur poisoning may have occurred in the sensor, the sulfur poisoning in the sensor can be eliminated. It may be said in this case that a parameter for determining the need for sulfur poisoning recovery control is calculated as the SOx related parameter.

In the control apparatus described above, the parameter calculation voltage may be a voltage that is equal to or higher than 0.8 V. According to this configuration, an output current corresponding to the amount of SOx can be output from the sensor during the voltage reduction control. As a result, the SOx related parameter can be calculated with a high degree of precision.

In the control apparatus described above, the applied voltage upon completion of the voltage reduction control may be less than 0.7 V. According to this configuration, an output current corresponding to the amount of SOx can be output from the sensor during the voltage reduction control. As a result, the SOx related parameter can be calculated with a high degree of precision.

In the control apparatus described above, the electronic control unit may be configured to apply a first voltage that is lower than the parameter calculation voltage steadily to the sensor, and detect the oxygen concentration of the detection subject gas using the output current of the sensor obtained when the first voltage is applied to the sensor. According to this configuration, the oxygen concentration of the detection subject gas can be detected.

The electronic control unit preferably uses a peak value of the output current obtained during the voltage reduction control as the output current from which to calculate the parameter. The peak value is a minimum output current (or a maximum output current) of the output currents obtained during the voltage reduction control. It may therefore be said that the peak value is an output current that corresponds with a high degree of precision to the SOx related parameter. Hence, by using the peak value as the output current from which to calculate the SOx related parameter, the SOx related parameter can be calculated with an even higher degree of precision.

A third aspect of the invention is a control method for an internal combustion engine having a limiting current sensor, including: calculating a parameter relating to SOx contained in a detection subject gas using an output current of the sensor obtained when voltage reduction control is implemented to reduce an applied voltage applied to the sensor from a parameter calculation voltage; and implementing the voltage reduction control when an oxygen concentration of the detection subject gas is less than a predetermined concentration.

A fourth aspect of the invention is a control method for an internal combustion engine having a limiting current sensor, including: calculating a parameter relating to SOx contained in a detection subject gas using an output current of the sensor obtained when voltage reduction control is implemented to reduce an applied voltage applied to the sensor from a parameter calculation voltage; and implementing the voltage reduction control when a low oxygen concentration condition, according to which an oxygen concentration of the detection subject gas is predicted to be less than a predetermined concentration, is established.

According to the configurations described above, the oxygen concentration of the detection subject gas during the voltage reduction control is low. When the oxygen concentration of the detection subject gas during the voltage reduction control is low, a small proportion of the output current obtained during the voltage reduction control is occupied by an output current generated as a result of the oxygen concentration of the detection subject gas. Accordingly, a large proportion of the value of the output current obtained during the voltage reduction control is occupied by an output current generated as a result of the amount of SOx in the detection subject gas. In other words, the output current obtained during the voltage reduction control corresponds to the amount of SOx. Therefore, the SOx related parameter (i.e. a parameter relating to SOx) can be calculated with a high degree of precision.

BRIEF DESCRIPTION OF THE DRAWINGS

Features, advantages, and technical and industrial significance of exemplary embodiments of the invention will be described below with reference to the accompanying drawings, in which like numerals denote like elements, and wherein:

FIG. 26 shows an example of a circuit employed in the limiting current sensor of FIG. 1.

DETAILED DESCRIPTION OF EMBODIMENTS

A control apparatus for an internal combustion engine according to the invention will now be described with reference to the drawings. Embodiments of the invention will be described below using as an example a case in which exhaust gas discharged from the internal combustion engine is employed as a detection subject gas and a SOx concentration is employed as a SOx related parameter.

Figure 1:
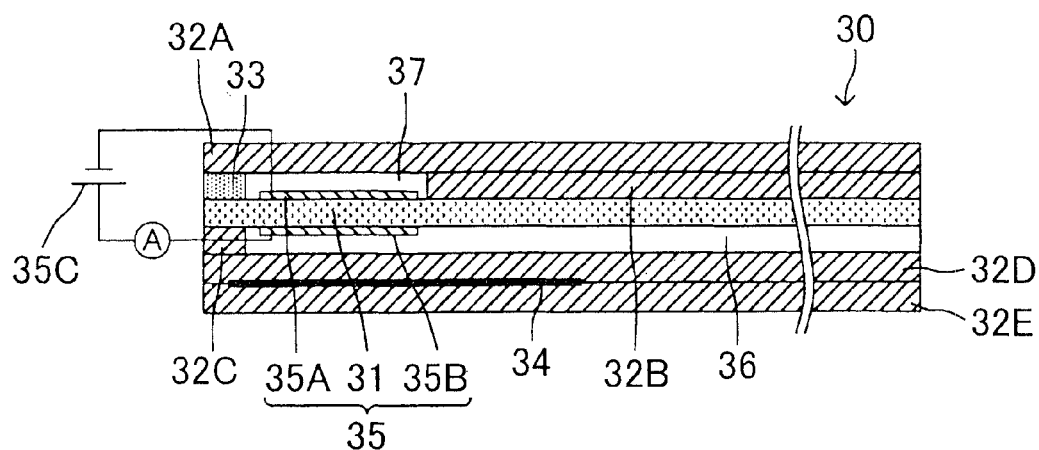
FIG. 1 shows a limiting current sensor (a single cell type limiting current sensor) according to an embodiment of the invention.

FIG. 1 shows a limiting current sensor 30 according to a first embodiment of the invention. The limiting current sensor 30 shown in FIG. 1 is a single cell type limiting current sensor. The limiting current sensor 30 shown in FIG. 1 includes a solid electrolyte layer 31, a first alumina layer 32A, a second alumina layer 32B, a third alumina layer 32C, a fourth alumina layer 32D, a fifth alumina layer 32E, a diffusion controlling layer 33, a heater 34, a sensor cell 35, a first sensor electrode 35A, a second sensor electrode 35B, a sensor cell voltage source 35C, an atmosphere introduction passage 36, and an interior space 37.

The solid electrolyte layer 31 is constituted by zirconia or the like, and possesses oxygen ion conductivity. The alumina layers 32A to 32E are constituted by alumina. The diffusion controlling layer 33 is a porous layer through which the exhaust gas can pass. In the limiting current sensor (also referred to simply as the sensor hereafter) 30 shown in FIG. 1, the respective layers are laminated in ascending order of the fifth alumina layer 32E, the fourth alumina layer 32D, the third alumina layer 32C, the solid electrolyte layer 31, the diffusion controlling layer 33 and the second alumina layer 32B, and the first alumina layer 32A. The heater 34 is disposed between the fourth alumina layer 32D and the fifth alumina layer 32E.

The atmosphere introduction passage 36 is a space defined by the solid electrolyte layer 31, the third alumina layer 32C, and the fourth alumina layer 32D such that a part thereof is open to the atmosphere. The interior space 37 is a space defined by the first alumina layer 32A, the solid electrolyte layer 31, the diffusion controlling layer 33, and the second alumina layer 32B such that a part thereof communicates with the exterior of the sensor via the diffusion controlling layer 33.

The first sensor electrode 35A and the second sensor electrode 35B are constituted by platinum, a platinum group element such as rhodium, or an alloy thereof. The first sensor electrode 35A is disposed on a wall surface on one side of the solid electrolyte layer 31. In other words, the first sensor electrode 35A is disposed on the wall surface of the solid electrolyte layer 31 forming the interior space 37. The second sensor electrode 35B is disposed on a wall surface on the other side of the solid electrolyte layer 31. In other words, the second sensor electrode 35B is disposed on the wall surface of the solid electrolyte layer 31 forming the atmosphere introduction passage 36. The electrodes 35A, 35B and the solid electrolyte layer 31 together constitute the sensor cell 35. The sensor 30 is configured to be capable of applying a voltage to the sensor cell 35 from the sensor cell voltage source 35C. More specifically, the sensor 30 is configured to be capable of applying a voltage between the first sensor electrode 35A and the second sensor electrode 35B from the sensor cell voltage source 35C. The first sensor electrode 35A is a cathode side electrode, and the second sensor electrode 35B is an anode side electrode.

When a voltage is applied to the sensor cell 35 and SOx in the interior space 37 contacts the first sensor electrode 35A, the SOx is broken down on the first sensor electrode 35A such that oxygen in the SOx forms oxygen ions. The oxygen ions move through the solid electrolyte layer 31 toward the second sensor electrode 35B. At this time, a current that is commensurate with the amount of oxygen ions moving through the interior of the solid electrolyte layer 31 flows between the first sensor electrode 35A and the second sensor electrode 35B. When the oxygen ions reach the second sensor electrode 35B, the oxygen ions turn into oxygen in the second sensor electrode 35B and are discharged into the atmosphere introduction passage 36.

Figure 2:
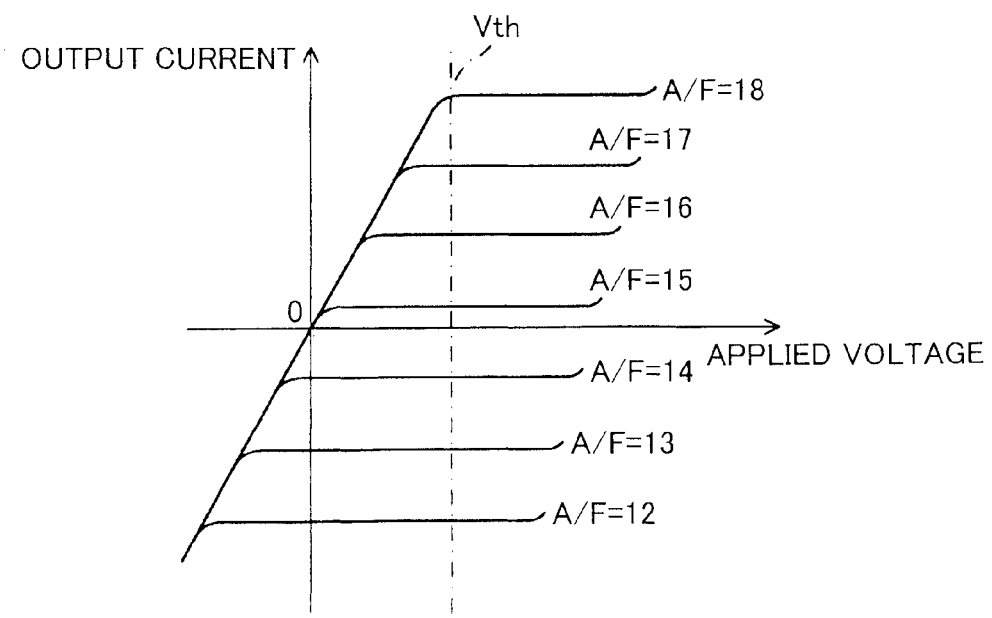
FIG. 2 shows an output characteristic of the limiting current sensor of FIG. 1.

FIG. 2 shows a relationship between a sensor cell applied voltage and a sensor cell output current in the limiting current sensor according to the first embodiment. The sensor cell applied voltage is the voltage applied to the sensor cell 35 by the sensor cell voltage source 35C. The sensor cell output current is the current flowing between the first sensor electrode 35A and the second sensor electrode 35B. In FIG. 2, a line indicated by A/F=12 shows variation in the sensor cell output current relative to variation in the sensor cell applied voltage when an air-fuel ratio of the exhaust gas is 12. Similarly, lines indicated by A/F=13 to A/F=18 respectively show variation in the sensor cell output current relative to variation in the sensor cell applied voltage when the air-fuel ratio of the exhaust gas is 13 to 18.

As shown in FIG. 2, in a case where the air-fuel ratio of the exhaust gas is 18, for example, in a range where the sensor cell applied voltage is smaller than a certain value Vth, (i) an absolute value of the sensor cell output current decreases as the sensor cell applied voltage increases when the sensor cell output current takes a negative value, and (ii) the absolute value of the sensor cell output current increases as the sensor cell applied voltage increases when the sensor cell output current takes a positive value. In a fixed range where the sensor cell applied voltage equals or exceeds the certain value Vth, the sensor cell output current takes a constant value irrespective of the sensor cell applied voltage.

A similar relationship is established between the sensor cell applied voltage and the sensor cell output current when the air-fuel ratio of the exhaust gas is between 12 and 17. As is evident from FIG. 2, at all of the detected air-fuel ratios, when a voltage at which the sensor cell output current remains constant irrespective of the sensor cell applied voltage is applied to the sensor cell 35, the air-fuel ratio of the exhaust gas can be detected on the basis of the sensor cell output current detected at that time. In other words, the limiting current sensor 30 according to the first embodiment can be used to detect the air-fuel ratio of the exhaust gas. The air-fuel ratio of the exhaust gas is a parameter having a correlative relationship with an oxygen concentration of the exhaust gas, and therefore, it may be said that the limiting current sensor according to the first embodiment is capable in principle of detecting the oxygen concentration of the exhaust gas.

According to the researches of the inventors of the present application, it is newly found that a current corresponding to the concentration of Sox in exhaust gas is obtained from the limiting current sensor by reducing the voltage applied to the limiting current sensor from a predetermined voltage (hereinafter, "SOx concentration detection voltage"). The voltage applied to the limiting current sensor is the voltage applied to the sensor cell 35 from the sensor cell voltage source 35C. In the following description, the output current refers to the current output from the sensor cell 35, and the oxygen concentration of the exhaust gas remains constant at 1%.

Figure 3:
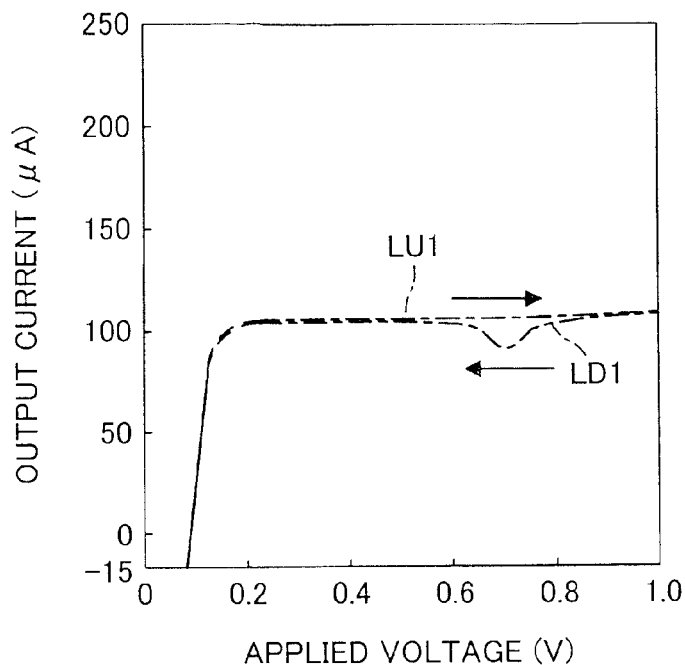
FIG. 3 shows an output characteristic of the limiting current sensor of FIG. 1.

FIG. 3 shows variation in the output current when the applied voltage is gradually increased from 0.1 V to 1.0 V and then gradually reduced from 1.0 V to 0.1 V. The abscissa in FIG. 3 shows the applied voltage, and the ordinate in FIG. 3 shows the output current.

In FIG. 3, a dot-dash line LU1 shows variation in the output current when the applied voltage is increased from 0.1 V to 1.0 V in a case where the exhaust gas contains SOx. A dot-dash line LD1 in FIG. 3 shows variation in the output current when the applied voltage is reduced from 1.0 V to 0.1 V likewise in a case where the exhaust gas contains SOx.

As shown by the dot-dash line LU1 in FIG. 3, when the applied voltage is increased from 0.1 V to approximately 0.2 V in a case where the exhaust gas contains SOx, the output current increases rapidly to approximately 100 μA. As the applied voltage increases from approximately 0.2 V to approximately 0.6 V, the output current remains substantially constant at approximately 100 μA. When the applied voltage exceeds approximately 0.6 V, the output current starts to increase. As the applied voltage increases from approximately 0.6 V to 1.0 V, the output current increases gradually, albeit slightly, and when the applied voltage reaches 1.0 V, the output current reaches approximately 105 μA.

As shown by the dot-dash line LD1 in FIG. 3, when the applied voltage is gradually reduced from 1.0 V toward 0.4 V thereafter, the output current decreases gradually from approximately 105 μA, and as the applied voltage falls from approximately 0.8 V to approximately 0.7 V, the output current decreases rapidly so as to reach approximately 80 μA. As the applied voltage falls from approximately 0.7 V to 0.4 V, the output current increases rapidly, and when the applied voltage reaches 0.4 V, the output current is approximately 100 μA.

Hence, when the applied voltage is increased from 0.4 V to 0.8 V and then reduced from 0.8 V to 0.4 V in a case where the exhaust gas contains SOx, the output current decreases rapidly and then increases rapidly as the applied voltage is reduced. In other words, when the applied voltage is reduced from 0.8 V to 0.4 V, the output current exhibits variation including a minimum value (in other words, a peak value). Referring to FIG. 3, the output current takes the peak value when the applied voltage reaches approximately 0.7 V.

In a case where the exhaust gas contains SOx, the output current over a period extending from a point at which the applied voltage rises above approximately 0.6 V to a point at which the applied voltage reaches 1.0 V is larger than the output current over the period, extending from the point at which the applied voltage rises above approximately 0.6 V to the point at which the applied voltage reaches 1.0 V in a case where the exhaust gas does not contain SOx.

Figure 4:
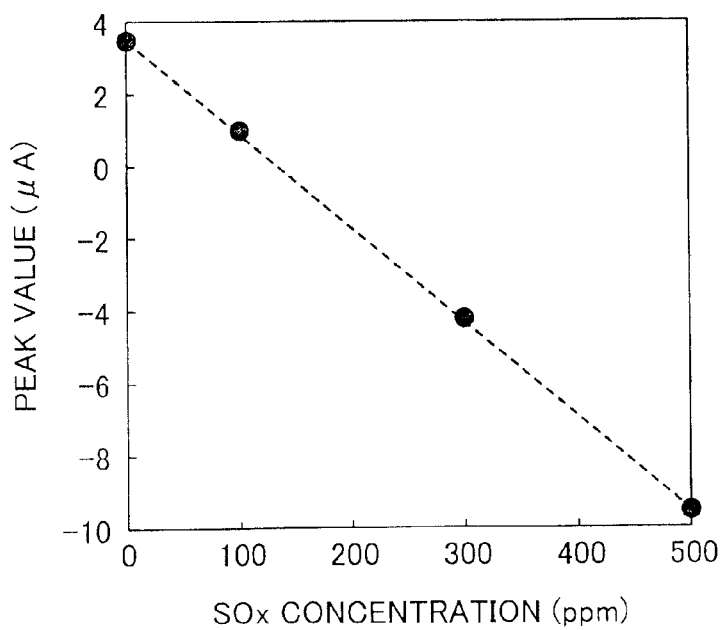
FIG. 4 shows a relationship between a SOx concentration and a peak value of an output current.

According to the researches of the inventors of the present application, it is found that there is the correlation shown in FIG. 4 between the peak value of output current and the concentration of SOx at the time when the applied voltage is reduced from 0.8 V to 0.4 V as described above in a single cell type limiting current sensor. In other words, it was found that the SOx concentration of the exhaust gas increases as a difference between a reference current (i.e. the output current at a point where the applied voltage reaches 0.8 V) and the peak value increases. The single cell type limiting current sensor according to the first embodiment can be used to detect the oxygen concentration of the exhaust gas, and accordingly the air-fuel ratio of the exhaust gas. Hence, with the single cell type limiting current sensor according to the first embodiment, it is possible to calculate (detect) the SOx concentration using the aforesaid peak value by employing a sensor that can be used to detect the oxygen concentration of exhaust gas.

Figure 5:
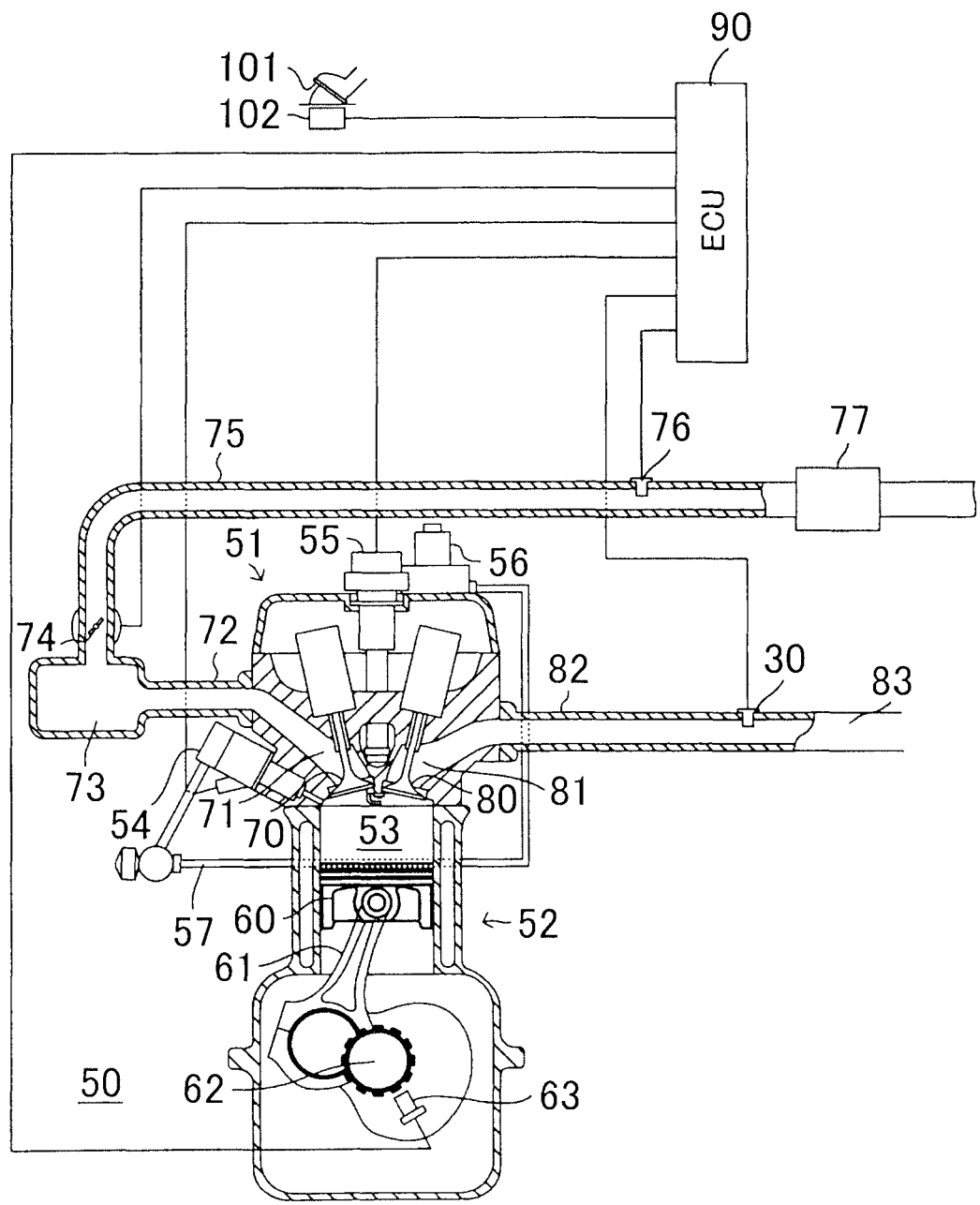
FIG. 5 shows an internal combustion engine including a SOx concentration detection apparatus having the limiting current sensor of FIG. 1.

FIG. 5 shows an internal combustion engine including a SOx concentration detection apparatus having the limiting current sensor 30 of FIG. 1. The internal combustion engine of FIG. 5 is a spark ignition internal combustion engine (a so-called gasoline engine). However, the invention may also be applied to a compression self-ignition internal combustion engine (a so-called diesel engine). The internal combustion engine in FIG. 5 is operated at the stoichiometric air-fuel ratio in most engine operation regions.

An internal combustion engine 50 having the limiting current sensor 30, shown in FIG. 5, includes a cylinder head 51, a cylinder block 52, a combustion chamber 53, a fuel injection valve 54, a spark plug 55, a fuel pump 56, a fuel supply pipe 57, a piston 60, a connecting rod 61, a crankshaft 62, a crank angle sensor 63, an intake valve 70, an intake port 71, an intake manifold 72, a surge tank 73, a throttle valve 74, an intake pipe 75, an air flow meter 76, an air filter 77, an exhaust valve 80, an exhaust port 81, an exhaust manifold 82, an exhaust pipe 83, an electronic control unit (ECU) 90, an accelerator pedal 101, and an accelerator pedal depression amount sensor 102.

The fuel injection valve 54, the spark plug 55, the throttle valve 74, the crank angle sensor 63, the air flow meter 76, the accelerator pedal depression amount sensor 102, and the limiting current sensor 30 are electrically connected to the ECU 90. The ECU 90 transmits signals for operating the fuel injection valve 54, the spark plug 55, and the throttle valve 74 thereto. The ECU 90 receives signals from the crank angle sensor 63, the air flow meter 76, and the accelerator pedal depression amount sensor 102. A signal corresponding to a rotation speed of the crankshaft 62 is output from the crank angle sensor 63. The ECU 90 calculates an engine rotation speed on the basis of the signal received from the crank angle sensor 63. A signal corresponding to a flow rate of air passing through the intake pipe 75 (or a flow rate of air taken into the combustion chamber 53) is output from the air flow meter 76. The ECU 90 calculates, an intake air amount on the basis of the signal from the air flow meter 76. A signal corresponding to a depression amount of the accelerator pedal 101 is output from the accelerator pedal depression amount sensor 102. The ECU 90 calculates an engine load on the basis of the signal received from the accelerator pedal depression amount sensor 102.

The limiting current sensor 30 is attached to the exhaust pipe 83. Hence, a gas (in other words, a detection subject gas) serving as a detection subject of the limiting current sensor 30 is exhaust gas discharged from the combustion chamber 53. The limiting current sensor 30 outputs a current corresponding to the SOx concentration of the exhaust gas arriving therein. The ECU 90 calculates the SOx concentration on the basis of the current received from the limiting current sensor 30. A calculation method will be described in detail below.

Figure 6:
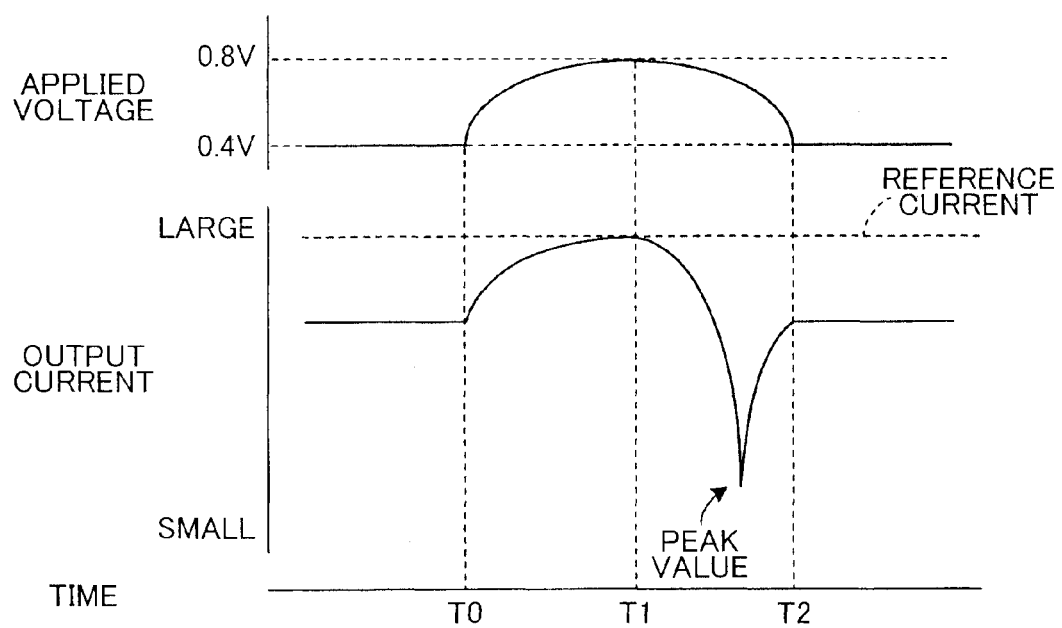
FIG. 6 is a time chart showing an output current corresponding to variation in an applied voltage, according to a first embodiment.

SOx concentration detection according to the first embodiment will now be described with reference to FIG. 6. In the first embodiment, the voltage applied to the sensor 30 is kept steady at 0.4 V (see a period up to a time T0 in FIG. 6). During the SOx concentration detection according to the first embodiment, the applied voltage is, increased from 0.4 V to 0.8 V (see a period extending from the time T0 to a time T1 in FIG. 6) and then reduced from 0.8 V to 0.4 V (see a period extending from the time T1 to a time T2 in FIG. 6). At this time, the ECU calculates (detects) the SOx concentration while the applied voltage is reduced from 0.8 V to 0.4 V using the peak value of the output current input into the ECU and the reference current. The calculated SOx concentration increases steadily as the difference between the reference current and the peak value increases.

In this embodiment, when the SOx concentration is calculated using the difference (hereinafter, "current difference") between the peak value and the reference current, a SOx concentration corresponding to a current difference is determined in advance for each current difference by experiment or the like, for example. The SOx concentrations determined in advance are stored in the ECU in the form of a map of a current difference function, and the SOx concentration is calculated by reading the SOx concentration corresponding to the current difference calculated during the SOx concentration detection from the map.

The limiting current sensor of the SOx concentration detection apparatus according to the first embodiment can be used to detect the oxygen concentration of the exhaust gas (or the air-fuel ratio of the exhaust gas). Hence, with the SOx concentration detection apparatus according to the first embodiment, the SOx concentration of the exhaust gas can be detected using a sensor that can be used to detect the oxygen concentration of exhaust gas. In other words, when the applied voltage is maintained at a constant voltage (0.4 V, for example) or the applied voltage is increased, the SOx affects the output current to a smaller degree than other components ($O_2$ and NOx, for example). However, the inventors of this application have found that when the applied voltage is reduced from a parameter detection voltage (0.8 V, for example), the SOx affects the output current to a greater degree than the other components. Therefore, with the SOx concentration detection apparatus according to the first embodiment, the SOx concentration can be detected with a high degree of precision using a sensor that can be used to detect the oxygen concentration of exhaust gas.

The peak value is an output current, from among output currents obtained as the applied voltage is reduced, that differs most greatly from an output current obtained when the SOx concentration is zero. It may therefore be said that the peak value is an output current that corresponds to the SOx concentration with a high degree, of precision. Hence, by employing the peak value as the output current used to detect the SOx concentration, the SOx concentration can be detected with an even higher degree of precision.

In the first embodiment, the voltage applied to the sensor before starting to reduce the applied voltage is 0.4 V. This voltage is lower than the applied voltage of 0.8 V at the start of applied voltage reduction. According to the first embodiment, therefore, an amount of power consumed during the SOx concentration detection can be reduced in comparison with a case where the voltage applied to the sensor before the start of applied voltage reduction is 0.8 V.

Oxygen concentration control according to the first embodiment will now be described. In the following description, voltage increase control is control executed during the SOx concentration detection to increase the voltage applied to the sensor from 0.4 V to 0.8 V. Further, voltage reduction control is control executed during the SOx concentration detection to reduce the voltage applied to the sensor from 0.8 V to 0.4 V.

In the SOx concentration detection according to the first embodiment, when the SOx concentration detection is requested, or in other words when implementation of the voltage increase control is requested, the voltage increase control is implemented while implementing oxygen concentration control. Oxygen concentration control is control for controlling the oxygen concentration of the exhaust gas at or below a predetermined concentration.

The predetermined concentration of the oxygen concentration of the exhaust gas is an oxygen concentration of the exhaust gas at which a proportion of an oxygen output current is much smaller than a proportion of a SOx output current, for example zero (or substantially zero). The proportion of the oxygen output current is a proportion of the output current obtained during the voltage reduction control that is occupied by an output current generated as a result of the oxygen in the exhaust gas. The proportion of the SOx output current is a proportion of the output current obtained during the voltage reduction control that is occupied by an output current generated as a result of the SOx in the exhaust gas.

Figure 8:
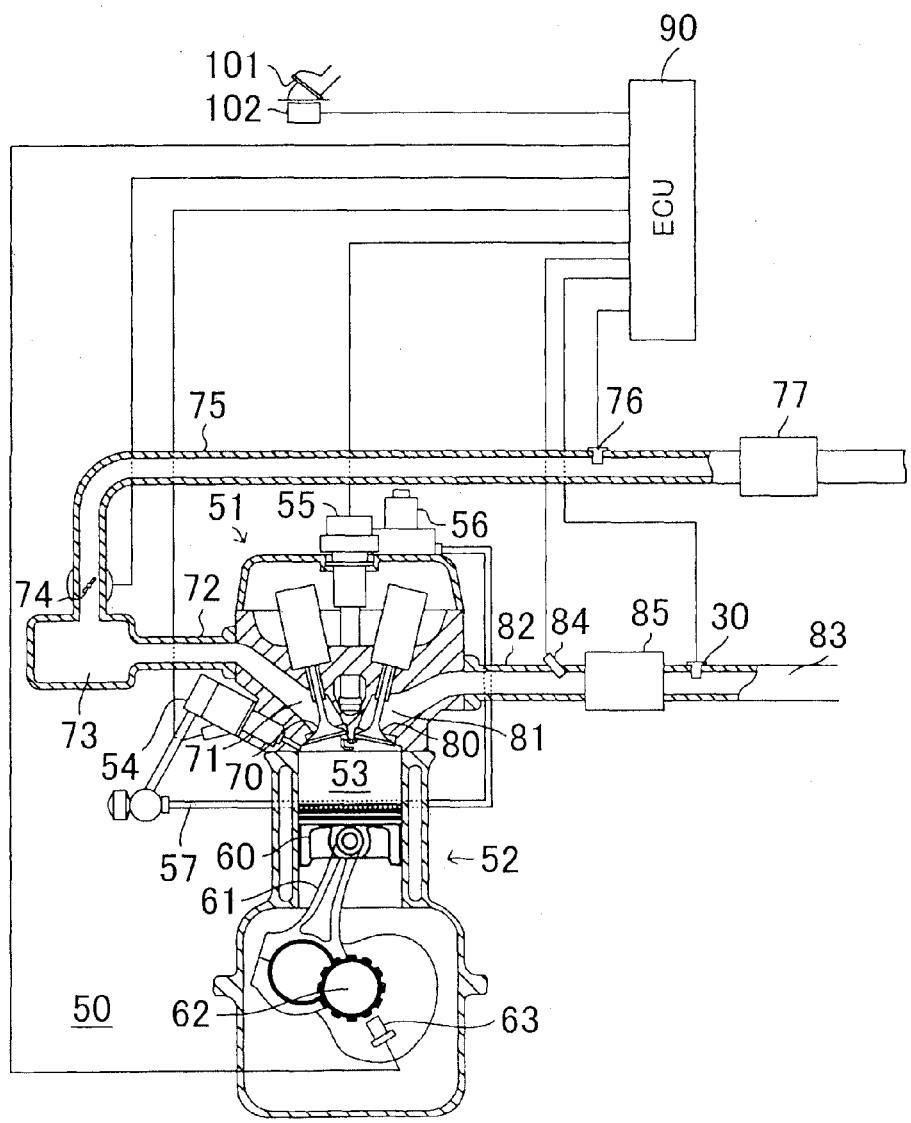
FIG. 8 shows the internal combustion engine that includes the SOx concentration detection apparatus having the limiting current sensor of FIG. 1.

For example, the oxygen concentration control is control for increasing an EGR rate by increasing an EGR valve opening, or control for implementing a post injection, or control for implementing exhaust addition in an internal combustion engine shown in FIG. 8.

In the internal combustion engine shown in FIG. 8, an exhaust gas purification catalyst 85 that purifies components of the exhaust gas is attached to an exhaust pipe 83. The exhaust gas purification catalyst 85 has at least an oxidation capacity. A fuel addition valve 84 that adds fuel to the exhaust gas flowing through, the exhaust pipe 83 is attached to the exhaust pipe 83 upstream of the exhaust gas purification catalyst 85. The fuel addition valve 84 is electrically connected to the ECU 90. The ECU 90 controls an operation of the fuel addition valve 84. The control for implementing exhaust addition is control for adding fuel to the exhaust gas from the fuel addition valve 84. The fuel added to the exhaust gas reacts with the oxygen in the exhaust gas due to the oxidation capacity of the exhaust gas purification catalyst 85, and is thereby burned. As a result, the oxygen in the exhaust gas is consumed such that the oxygen concentration of the exhaust gas decreases.

In the internal combustion engine shown in FIG. 8, the sensor 30 is attached to the exhaust pipe 83 downstream of the exhaust gas purification catalyst 85. However, when the fuel added to the exhaust gas from the fuel addition valve 84 reacts with the oxygen in the exhaust gas so as to burn regardless of the oxidation capacity of the exhaust gas purification catalyst 85, the sensor 30 may be attached to the exhaust pipe 83 upstream of the exhaust gas purification catalyst 85.

The SOx concentration detection according to the first embodiment will now be described with reference to FIG. 9. In the following description, a SOx concentration detection request flag is set when the SOx concentration detection is requested, and reset when the SOx concentration detection is completed.

Figure 9:
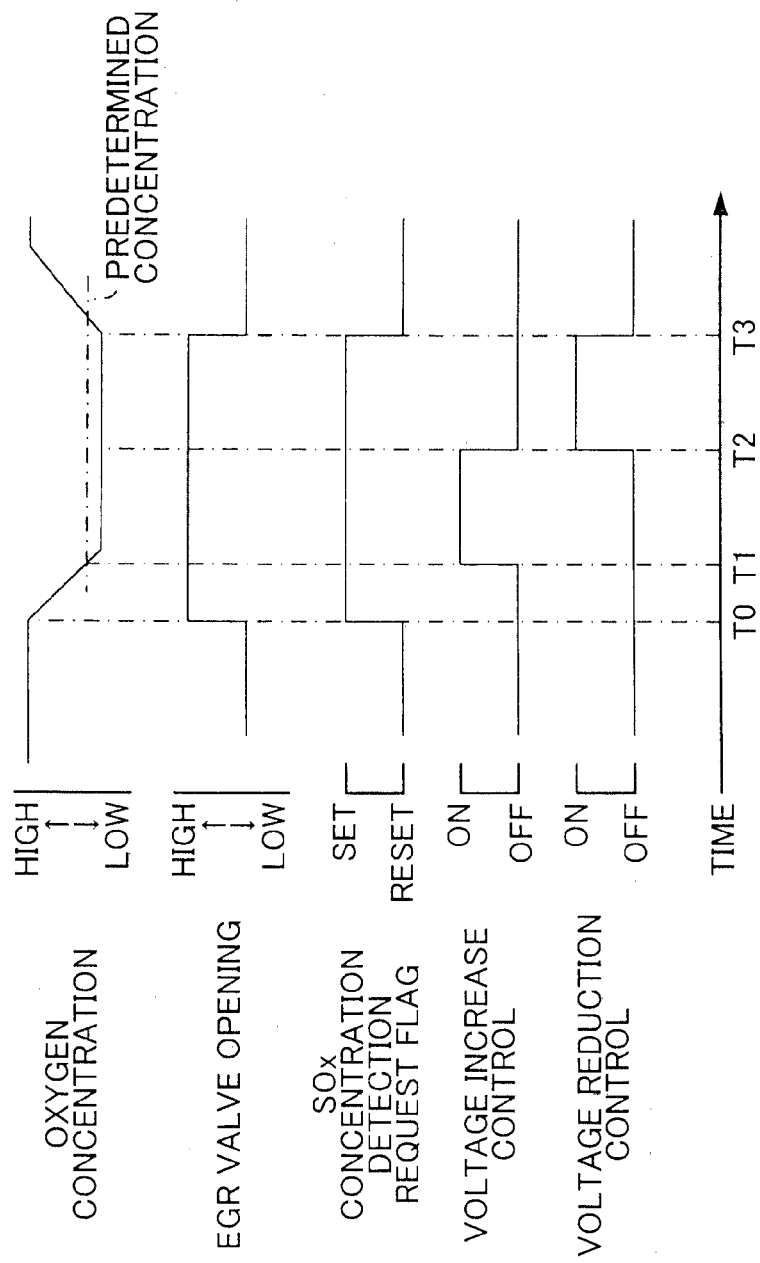
FIG. 9 is a time chart showing implementation of SOx concentration detection according to the first embodiment.

In the example of FIG. 9, up to a time T0, the oxygen concentration of the exhaust gas is higher than the predetermined concentration. Then, when the SOx concentration detection request flag is set at the time T0, the oxygen concentration control is implemented by increasing the EGR valve opening. As a result, the oxygen concentration of the exhaust gas gradually decreases. When the oxygen concentration of the exhaust gas falls to or below the predetermined concentration at a time T1, the voltage increase control is implemented. At a time T2, the voltage increase control is completed, and simultaneously, the voltage reduction control is implemented. When the voltage reduction control is completed at a time T3, the oxygen concentration control is terminated by returning the EGR valve opening to normal.

As a result, the oxygen concentration of the exhaust gas increases above the predetermined concentration.

With the SOx concentration detection according to the first embodiment, the SOx concentration can be calculated with a high degree of precision. A reason for this, will now be described. When the oxygen concentration of the exhaust gas is high during the voltage reduction control, the proportion of the oxygen concentration output current is large. In this case, the proportion of the SOx output current is smaller than the proportion of the oxygen concentration output current, and therefore the value of the output current obtained during the voltage reduction control is largely dependent on the oxygen concentration of the exhaust gas rather than the SOx concentration of the exhaust gas. In other words, it may be impossible to say that the SOx concentration calculated using the output current during the voltage reduction control corresponds accurately to the SOx concentration of the exhaust gas.

With the SOx concentration detection according to the first embodiment, on the other hand, the oxygen concentration of the exhaust gas is low during the voltage reduction control, and therefore the proportion of the oxygen concentration output current is small. Hence, the value of the output current obtained during the voltage reduction control is largely dependent on the SOx concentration of the exhaust gas rather than the oxygen concentration of the exhaust gas. In other words, the SOx concentration calculated using the output current during the voltage reduction control corresponds to the SOx concentration of the exhaust gas. As a result, with the SOx concentration detection according to the first embodiment, the SOx concentration can be calculated with a high degree of precision.

The concept of the SOx concentration detection according to the first embodiment may also be applied to calculation of a parameter relating to Sox, the output current proportion of which in the output current obtained during the voltage reduction control is smaller than the proportion of the oxygen concentration output current when the oxygen concentration of the exhaust gas is high.

In the SOx concentration detection according to the first embodiment, the applied voltage at the start, point of the voltage increase control (in other words, the applied voltage applied steadily to the sensor) is not limited to 0.4 V, and may be any voltage at which the output current varies so as to include the peak value when the applied voltage is reduced after being increased. For example, the applied voltage at the start point of the voltage increase control may be 0.6 V or smaller, but is preferably 0.4 V.

The applied voltage at the end point of the voltage increase control is not limited to 0.8 V, and may be any voltage at which the output current varies so as to include the peak value when the applied voltage is reduced after being increased, or any voltage at or above a maximum voltage of an output stability voltage range, for example 0.8 V or more. The output stability voltage range is a range in which the output current remains substantially constant regardless of the applied voltage when the SOx concentration is zero, for example a range of 0.2 V to 0.8 V.

The applied voltage at the end point of the voltage reduction control is not limited to 0.4 V, and may be any voltage at or below the applied voltage corresponding to the peak value. For example, the applied voltage at the end point of the voltage reduction control may be any voltage at or below 0.7 V, but is preferably 0.4 V. Accordingly, the applied voltage at the start point of the voltage increase control may be identical or different to the applied voltage at the end point of the voltage reduction control.

In the SOx concentration detection according to the first embodiment, the peak value is used, but instead, an output current in a range where the output current decreases rapidly or a range where the output current increases rapidly as the applied voltage is reduced from 0.8 V to 0.4 V may be used.

The oxygen concentration of the exhaust, gas flowing into the interior space of the sensor may vary as the applied voltage decreases. In this case, taking into consideration the fact that reducing the applied voltage requires a fixed amount of time, it may be said that the output current obtained when the applied voltage is 0.4 V reflects the oxygen concentration of the exhaust gas in the interior space of the sensor at the point where the peak value is output more accurately than the output current obtained when the applied voltage is 0.8 V. Hence, during the SOx concentration detection according to the first embodiment, when the applied voltage is reduced from 0.8 V to 0.4 V, the output current at the point where the applied voltage reaches 0.4 V (or the output current following the elapse of a predetermined time from this point) may be used as the reference current instead of the reference current described above. Thus, the SOx concentration can be detected with a high degree of precision even when the oxygen concentration of the exhaust gas varies as the applied voltage decreases.

In the first embodiment, instead of calculating the SOx concentration using the peak value and the reference current, the SOx concentration may be calculated using the peak value and a conversion coefficient. At this time, the calculated SOx concentration increases as the peak value increases in a negative direction. The conversion coefficient is a coefficient for converting the peak value into a SOx concentration in accordance with the relationship shown in FIG. 4. When the peak value appears as a positive value, the calculated SOx concentration increases as the peak value increases in a positive direction.

When, during the SOx concentration detection according to the first embodiment, an increase speed or a reduction speed (a sweep speed) of the applied voltage is too high, the peak value may not be output, or a peak value corresponding sufficiently to the SOx concentration may not be output, even after the applied voltage is reduced. Hence, in the SOx concentration detection according to the first embodiment, an applied voltage increase speed or reduction speed at which a peak value corresponding sufficiently to the SOx concentration is output in response to reduction of the applied voltage is selected.

Figure 7A:
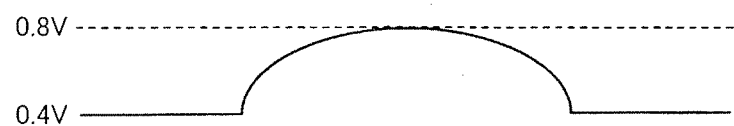
FIGS. 7A and 7B show how the applied voltage increases and decreases during SOx concentration detection.
Figure 7B:
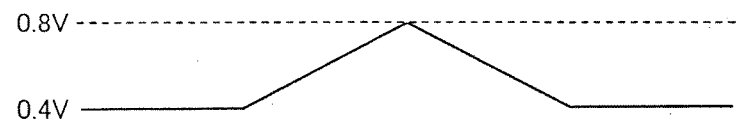

More specifically, as shown in FIG. 7A, the applied voltage is increased while gradually reducing the applied voltage increase speed and then reduced while gradually increasing the applied voltage reduction speed. Alternatively, as shown in FIG. 7B, the applied voltage is increased while maintaining the applied voltage increase speed at a fixed speed and then reduced while maintaining the applied voltage reduction speed at a fixed speed.

Even more specifically, in the SOx concentration detection according to the first embodiment, when variation in the applied voltage from the start of the voltage increase control to the end of the voltage reduction control is expressed as a frequency, the frequency is less than 100 Hz. To put it another way, a time from the start of the voltage increase control to the end of the voltage reduction control equals or exceeds 0.01 seconds.

Figure 10:
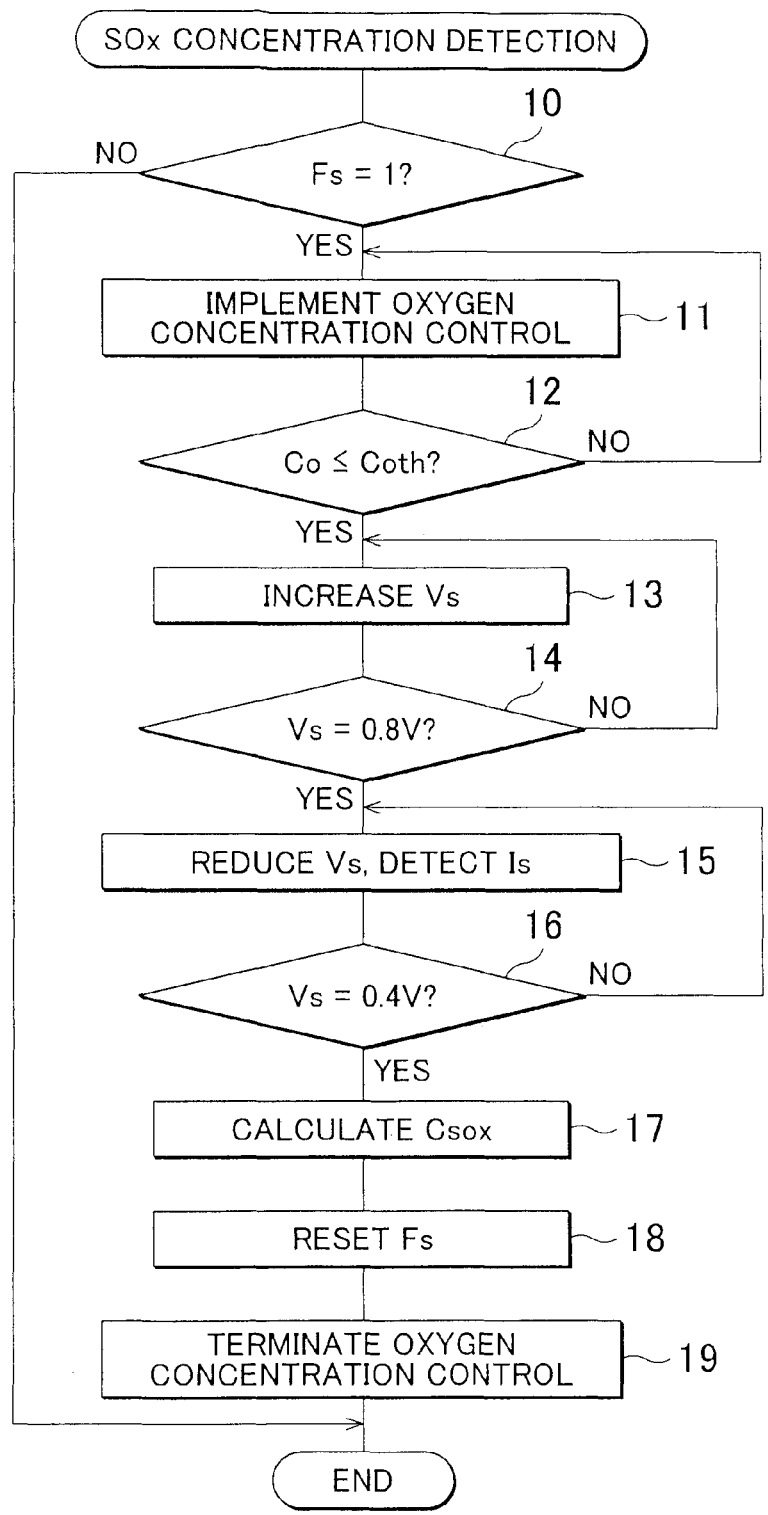
FIG. 10 shows an example of a SOx concentration detection flow according to the first embodiment.

An example of a flow of the SOx concentration detection according to the first embodiment will now be described with reference to FIG. 10. When the flow of FIG. 10 is started, the applied voltage is maintained at 0.4 V. In step 10, a determination is made as to whether or not a SOx concentration detection request flag Fs is set (Fs=1). When it is determined that Fs=1, the flow advances to step 11. When it is determined that Fs=1 is not established, on the other hand, the flow is terminated as is.

In step 11, oxygen concentration control is implemented. The oxygen concentration control is control for controlling the oxygen concentration of the exhaust gas at or below the predetermined concentration. Next, in step 12, a determination is made as to whether or not an oxygen concentration Co of the exhaust gas is less than a predetermined concentration Coth (Co≤Coth). Here, when it is determined that Co≤Coth, the flow advances to step 13. When it is determined that Co≤Coth is not established, on the other hand, the flow returns to step 11. Hence, the oxygen concentration control is continued until it is determined in step 12 that Co≤Coth.

In step 13, an applied voltage Vs is increased from 0.4 V toward 0.8 V. Next, in step 14, a determination is made as to, whether or not the applied voltage Vs has reached 0.8 V (Vs=0.8 V). Here, when it is determined that Vs=0.8 V, the flow advances to step 15. When it is determined that Vs=0.8 V is not established, on the other hand, the flow returns to step 13. Hence, the applied voltage Vs is increased continuously until it is determined in step 14 that Vs=0.8 V.

In step 15, the applied voltage Vs is reduced from 0.8 V toward 0.4 V, and an output current Is is detected. Next, in step 16, a determination is made as to whether or not the applied voltage Vs has reached 0.4 V (Vs=0.4 V). Here, when it is determined that Vs=0.4 V, the flow advances to step 17. When it is determined that Vs=0.4 V is not established, on the other hand, the flow returns to step 15. Hence, reduction of the applied voltage Vs and detection of the output current Is are continued until it is determined in step 16 that Vs=0.4 V.

In step 17, an SOx concentration Csox is calculated on the basis of the peak value of the output current Is detected in step 15. Next, in step 18, the SOx concentration detection request flag Fs is reset. Next, in step 19, the oxygen concentration control is terminated, whereupon the flow is terminated.

Next, SOx concentration detection according to a second embodiment will be described. Note that in the several embodiments to be described below, configurations and control not described are either identical to the configurations and control of the embodiments described in this specification, or are configurations and control that can be derived easily from the configurations and control of the embodiments described in this specification.

In the SOx concentration detection according to the second embodiment, when the SOx concentration detection is requested, or in other words when implementation of the voltage increase control is requested, the voltage increase control is implemented while implementing a low oxygen concentration operation. The low oxygen concentration operation is an operation of the internal combustion engine to be described below, in which the oxygen concentration of the exhaust gas is held at or below a predetermined concentration.

Figure 11:
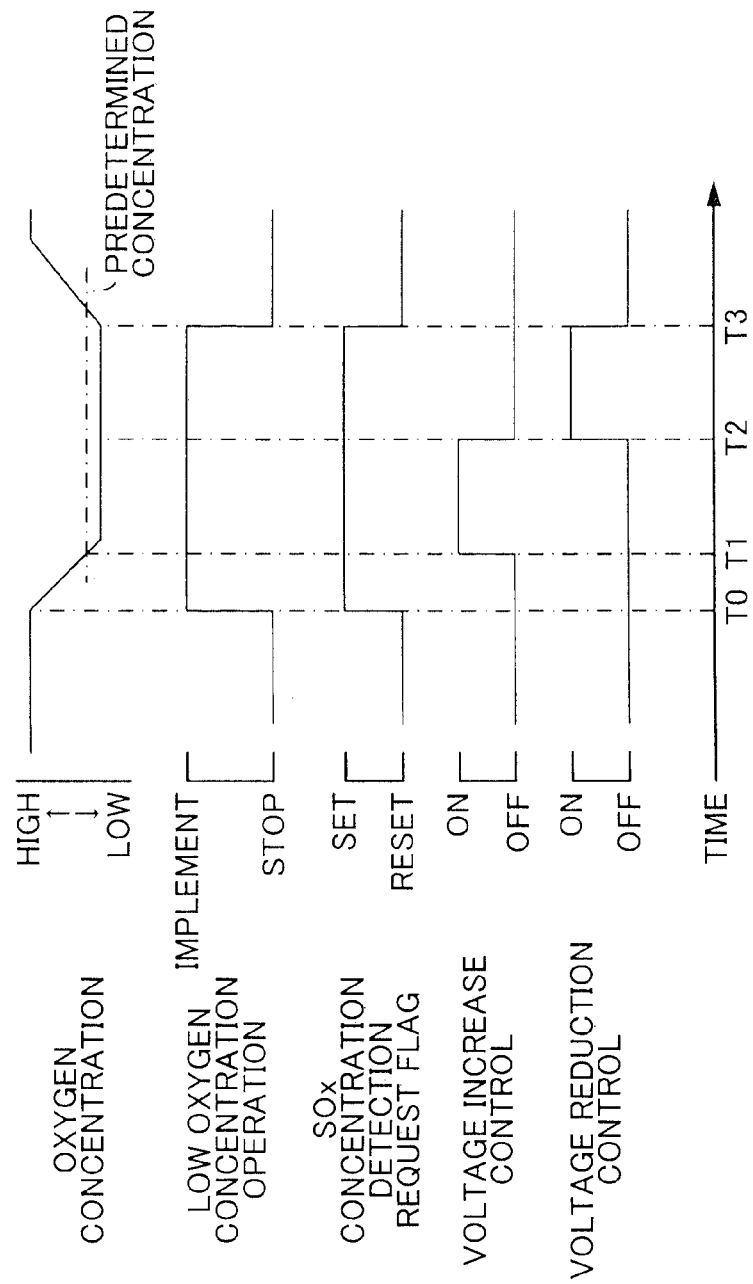
FIG. 11 is a time chart showing implementation of SOx concentration detection according to a second embodiment.

The SOx concentration detection according to the second embodiment will now be described with reference to FIG. 11. In the example shown in FIG. 11, the oxygen concentration of the exhaust gas is higher than the predetermined concentration up to a time T0. At the time T0, when the SOx concentration detection request flag is set, the low oxygen concentration operation is implemented such that the oxygen concentration of the exhaust gas decreases gradually. When the oxygen concentration of the exhaust gas falls to or below the predetermined concentration at a time T1, the voltage increase control is implemented. At a tune T2, the voltage increase control is completed, and simultaneously, the voltage reduction control is implemented. When the voltage reduction control is completed at a time T3, the low oxygen concentration operation is terminated. As a result, the oxygen concentration of the exhaust gas increases so as to rise above the predetermined concentration.

With the SOx concentration detection according to the second embodiment, the SOx concentration can be detected with a high degree of precision for identical reasons to the reasons described in relation to the first embodiment.

An example of a flow of the SOx concentration detection according to the second embodiment will now be described with reference to FIG. 12. Steps 23 to 28 in the flow of FIG. 12 are identical to steps 13 to 18 in the flow of FIG. 10, and therefore description of these steps has been omitted.

Figure 12:
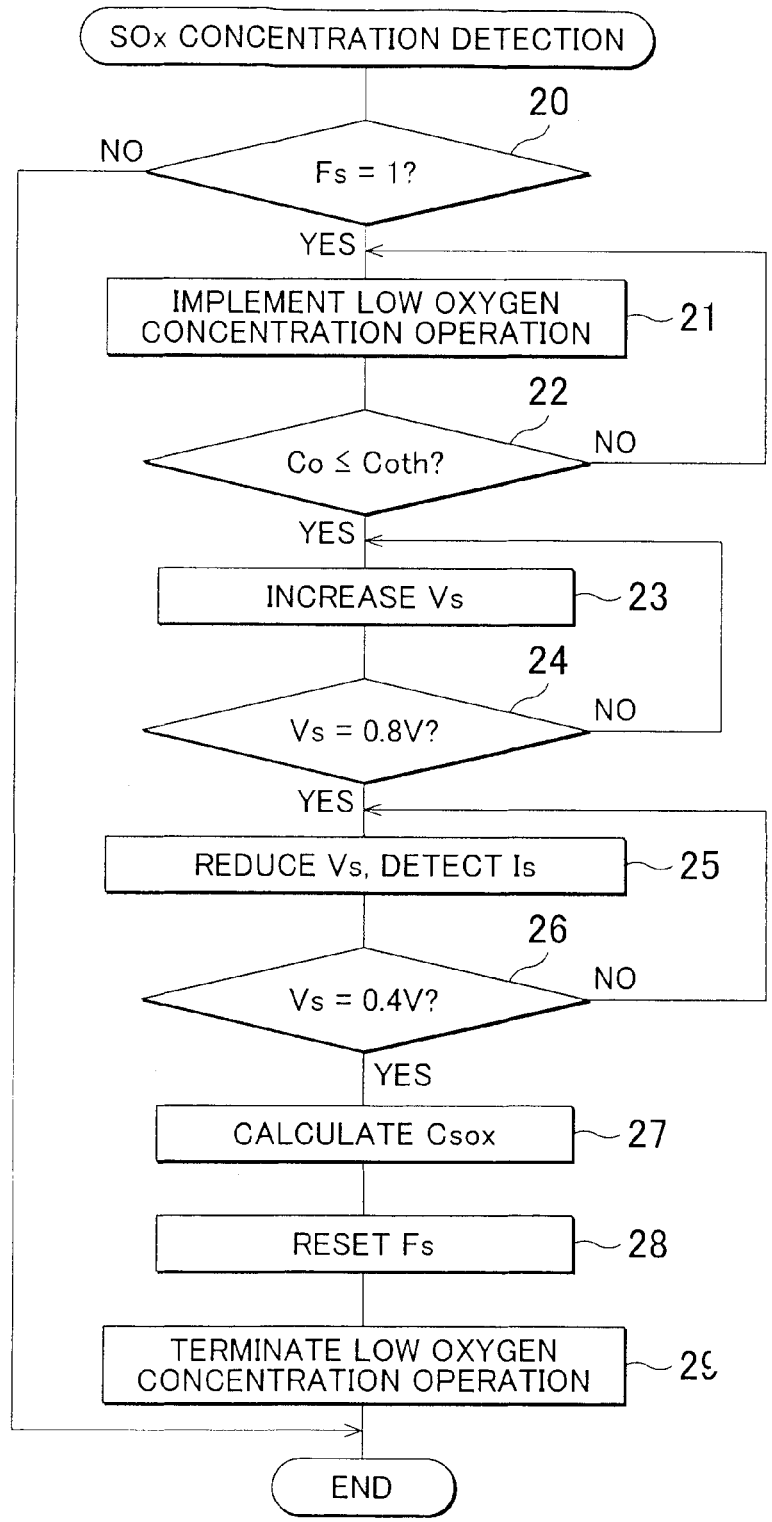
FIG. 12 shows an example of a SOx concentration detection flow according to the second embodiment.

When the flow of FIG. 12 is started, the applied voltage is maintained at 0.4 V. Then, in step 20, a determination is made as to whether or not the SOx concentration detection request flag Fs is set (Fs=1). When it is determined that Fs=1, the flow advances to step 21. Here, when it is determined that Fs=1 is not established, on the other hand, the flow is terminated as is.

In step 21, the low oxygen concentration operation is implemented. The low oxygen concentration operation is an operation in which the oxygen concentration of the exhaust gas is held at or below the predetermined concentration. Next, in step 22, a determination is made as to whether or not the oxygen concentration Co of the exhaust gas is less than the predetermined concentration Coth (Co≤Coth). Here, when it is determined that Co≤Coth, the flow advances to step 23. When it is determined that Co≤Coth is not established, on the other hand, the flow returns to step 21. Hence, the low oxygen concentration operation is continued until it is determined in step 22 that Co≤Coth.

In step 29, the low oxygen concentration operation is terminated, whereupon the flow is terminated.

Next, SOx concentration detection according to a third embodiment will be described. In this SOx concentration detection, the voltage increase control is implemented when the oxygen concentration of the exhaust gas falls to or below a predetermined concentration. In other words, the voltage increase control is implemented on condition that the oxygen concentration of the exhaust gas is less than the predetermined concentration.

Figure 13:
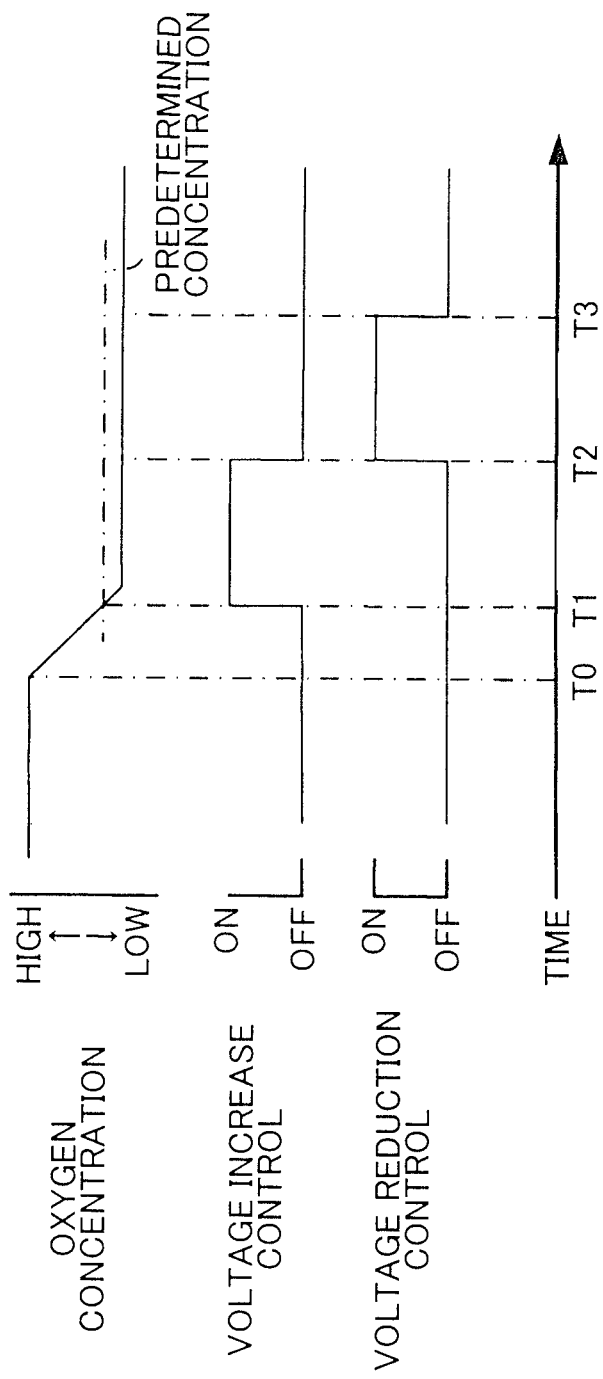
FIG. 13 is a time chart showing implementation of SOx concentration detection according to a third embodiment.

The SOx concentration detection according to the third embodiment will now be described with reference to FIG. 13. In the example shown in FIG. 13, the oxygen concentration of the exhaust gas is higher than the predetermined concentration up to a time T0. At the time T0, the oxygen concentration of the exhaust gas starts to decrease. When the oxygen concentration of the exhaust gas falls to or below the predetermined concentration at a time T1, the voltage increase control is implemented. At a time T2, the voltage increase control is completed, and simultaneously, the voltage reduction control is implemented. The voltage reduction control is completed at a time T3.

With the SOx concentration detection according to the third embodiment, the SOx concentration can be detected with a high degree of precision for identical reasons to the reasons described in relation to the first embodiment. Furthermore, with the SOx concentration detection according to the third embodiment, control is not performed actively to reduce the oxygen concentration of the exhaust gas at or below the predetermined concentration in order to detect the SOx concentration, and therefore the SOx concentration can be detected with a high degree of precision more easily.

In the third embodiment, the voltage increase control is implemented when the oxygen concentration of the exhaust gas falls to or below the predetermined concentration, regardless of whether or not the SOx concentration detection has been requested. However, the voltage increase control may be implemented when both the SOx concentration detection has been requested and the oxygen concentration of the exhaust gas has fallen to or below the predetermined concentration.

Figure 14:
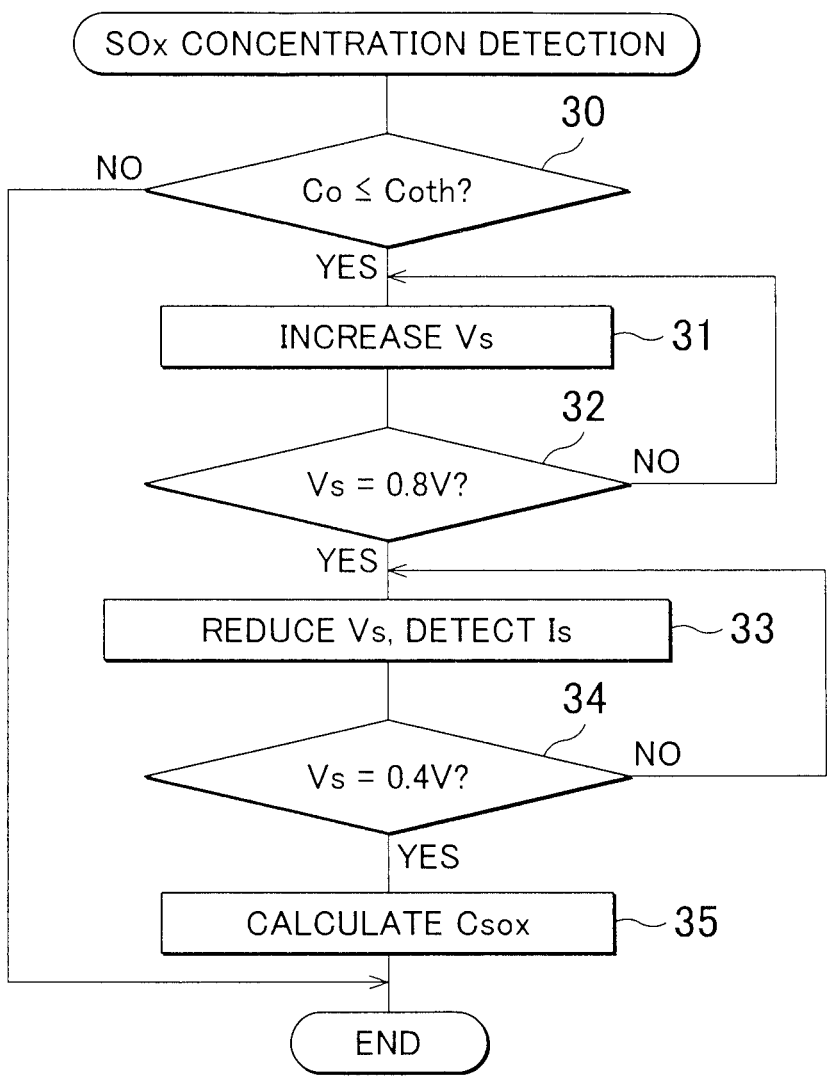
FIG. 14 shows an example of a SOx concentration detection flow according to the third embodiment.

An example of a flow of the SOx concentration detection according to the third embodiment will now be described with reference to FIG. 14. When the flow of FIG. 14 is started, the applied voltage is maintained at 0.4 V. Then, in step 30, a determination is made as to whether or not the oxygen concentration Co of the exhaust gas is less than the predetermined concentration Coth (Co≤Coth). Here, when it is determined that Co≤Coth, the flow advances to step 31. When it is determined that Co≤Coth is not established, on the other hand, the flow is terminated as is.

In step 31, the applied voltage Vs is increased from 0.4 V toward 0.8 V. Next, in step 32, a determination is made as to whether or not the applied voltage Vs has reached 0.8 V (Vs=0.8 V). When it is determined that Vs=0.8 V, the flow advances to step 33. When it is determined that Vs=0.8 V is not established, on the other hand, the flow returns to step 31. Hence, the applied voltage Vs is increased continuously until it is determined in step 32 that Vs=0.8 V.

In step 33, the applied voltage Vs is reduced from 0.8 V toward 0.4 V, and the output current Is is detected. Next, in step 34, a determination is made as to whether or not the applied voltage Vs has reached 0.4 V (Vs=0.4 V). Here, when it is determined that Vs=0.4 V, the flow advances to step 35. When it is determined that Vs=0.4 V is not established, on the other hand, the flow returns to step 33. Hence, reduction of the applied voltage Vs and detection of the output current Is are continued until it is determined in step 34 that Vs=0.4 V.

In step 35, the SOx concentration Csox is calculated on the basis of the peak value of the output current Is detected in step 33, whereupon the flow is terminated.

Next, voltage increase control according to a fourth embodiment will be described. In this voltage increase control, the voltage increase control is implemented when a low oxygen concentration operation is implemented. In other words, the voltage increase control is implemented when a low oxygen concentration condition according to which the oxygen concentration of the exhaust gas is predicted to be less than a predetermined concentration is established.

The low oxygen concentration operation is, for example, (i) an operation of the internal combustion engine in which the EGR rate equals or exceeds a predetermined EGR rate, (ii) an operation of the internal combustion engine in which the EGR valve opening equals or exceeds a predetermined opening, (iii) an operation of the internal combustion engine in which a post injection is implemented, (iv) an operation of the internal combustion engine in which exhaust addition is implemented, (v) an operation of the internal combustion engine in which particulate matter (PM) regeneration is implemented, (vi) an operation of the internal combustion engine in which NOx reduction is implemented, or (vii) an operation of the internal combustion engine in which rich combustion is implemented.

The PM regeneration described above is performed when a filter that collects particulate matter in the exhaust gas is disposed in the exhaust passage to burn the particulate matter collected in the filter by supplying unburned fuel to the filter. NOx reduction is performed when a catalyst for reducing and purifying NOx in the exhaust gas is disposed in the exhaust passage to reduce and purify the NOx in the exhaust gas by controlling the air-fuel ratio of the exhaust gas to a richer air-fuel ratio than the stoichiometric air-fuel ratio. In rich combustion, fuel is burned by setting the air-fuel ratio formed in the combustion chamber to a richer air-fuel ratio than the stoichiometric air-fuel ratio.

Figure 15:
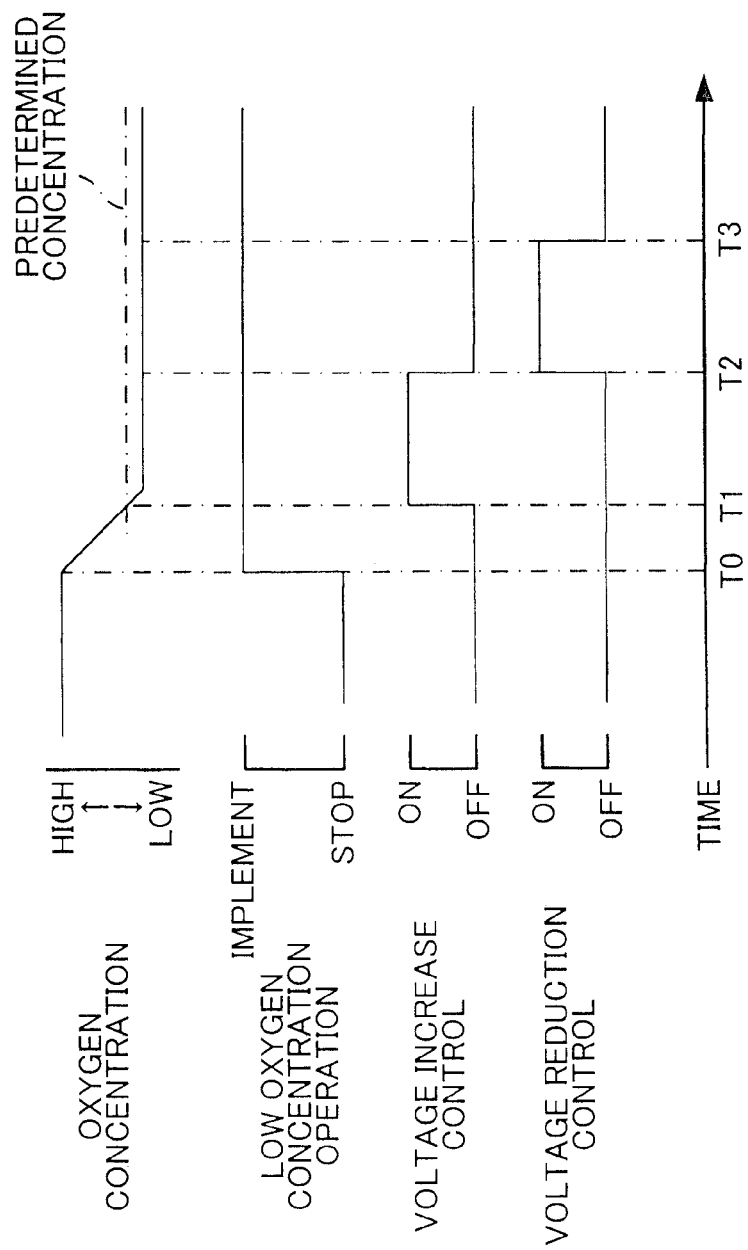
FIG. 15 is a time chart showing implementation of SOx concentration detection according to a fourth embodiment.

The SOx concentration detection according to the fourth embodiment will now be described with reference to FIG. 15. In the example shown in FIG. 15, the oxygen concentration of the exhaust gas is higher than the predetermined concentration up to a time T0. When the low oxygen concentration operation is implemented at the time T0, the oxygen concentration of the exhaust gas starts to decrease. When the oxygen concentration of the exhaust gas falls to or below the predetermined concentration at a time T1, following the elapse of a predetermined time from the time T0, the voltage increase control is implemented. At a time T2, the voltage increase control is completed, and simultaneously, the voltage reduction control is implemented. The voltage reduction control is completed at a time T3.

With the SOx concentration detection according to the fourth embodiment, the SOx concentration can be detected with a high degree of precision for identical reasons to the reasons described in relation to the first embodiment. Furthermore, the SOx concentration can be detected with a high degree of precision more easily for identical reasons to the reasons described in relation to the third embodiment.

In the fourth embodiment, the voltage increase control is implemented when the low oxygen concentration operation starts, regardless of whether or not the oxygen concentration of the exhaust gas has fallen to or below the predetermined concentration. However, the voltage increase control may be implemented after detecting the oxygen concentration of the exhaust gas and determining that the oxygen concentration of the exhaust gas has fallen to or below the predetermined concentration. Alternatively, the voltage increase control may be implemented after a sufficient amount of time for the oxygen concentration of the exhaust gas to fall to or below the predetermined concentration has elapsed following the start of the low oxygen concentration operation.

Figure 16:
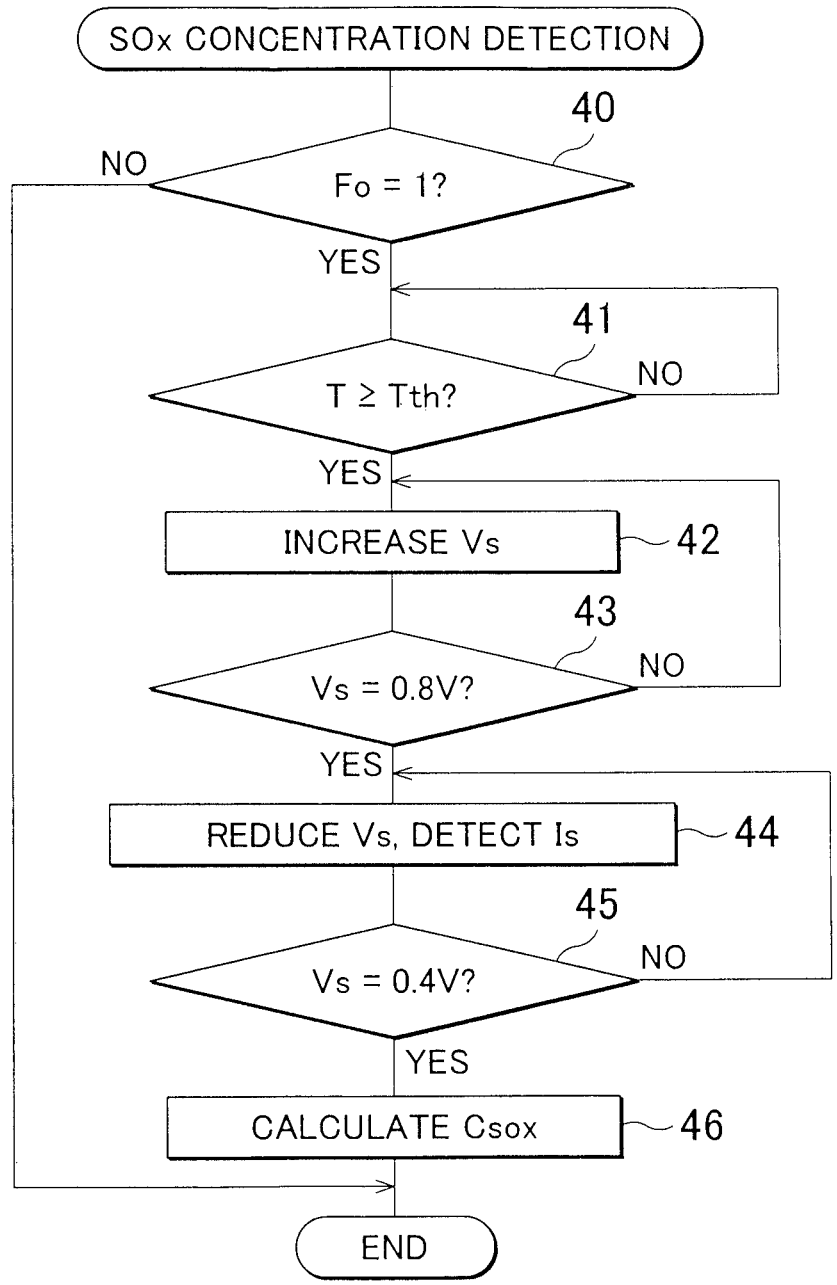
FIG. 16 shows an example of a SOx concentration detection flow according to the fourth embodiment.

An example of a flow of the SOx concentration detection according to the fourth embodiment will now be described with reference to FIG. 16. When the flow of FIG. 16 is started, the applied voltage is maintained at 0.4 V. Then, in step 40, a determination is made as to whether or not a low oxygen concentration operation flag Fo is set (Fo=1). The low oxygen concentration operation flag Fo is set when the low oxygen concentration operation is started, and reset when the low oxygen concentration operation is terminated. When it is determined in step 40 that Fo=1, the flow advances to step 41. When it is determined that Fo=1 is not established, on the other hand, the flow is terminated as is.

In step 41, a determination is made as to whether or not an elapsed time T following the start of the low oxygen concentration operation equals or exceeds a predetermined time Tth (T≥Tth). When it is determined that T≥Tth, the flow advances to step 42. When it is determined that T≥Tth is not established, on the other hand, the flow returns to step 41. Hence, step 41 is implemented repeatedly until it is determined in step 41 that T≥Tth.

In step 42, the applied voltage Vs is increased from 0.4 V toward 0.8 V Next, in step 43, a determination is made as to whether or not the applied voltage Vs has reached 0.8 V (Vs=0.8 V). Here, when it is determined that Vs=0.8 V, the flow advances to step 44. When it is determined that Vs=0.8 V is not established, on the other hand, the flow returns to step 42. Hence, the applied voltage Vs is increased continuously until it is determined in step 43 that Vs=0.8 V.

In step 44, the applied voltage Vs is reduced from 0.8 V toward 0.4 V, and the output current Is is detected. Next, in step 45, a determination is made as to whether or not the applied voltage Vs has reached 0.4 V (Vs=0.4 V). Here, when it is determined that Vs=0.4 V, the flow advances to step 46. When it is determined that Vs=0.4 V is not established, on the other hand, the flow returns to step 44. Hence, reduction of the applied voltage Vs and detection of the output current Is are continued until it is determined in step 45 that Vs=0.4 V.

In step 46, the SOx concentration Csox is calculated on the basis of the peak value of the output current Is detected in step 44. The flow is then terminated.

Next, SOx concentration detection according to a fifth embodiment will be described. In this SOx concentration detection, the voltage increase control is implemented when detection of the SOx concentration is requested. When the voltage increase control is complete, the voltage reduction control is implemented while implementing oxygen concentration control. Here, the oxygen concentration control is control for controlling the oxygen concentration of the exhaust gas at or below a predetermined concentration.

Figure 17:
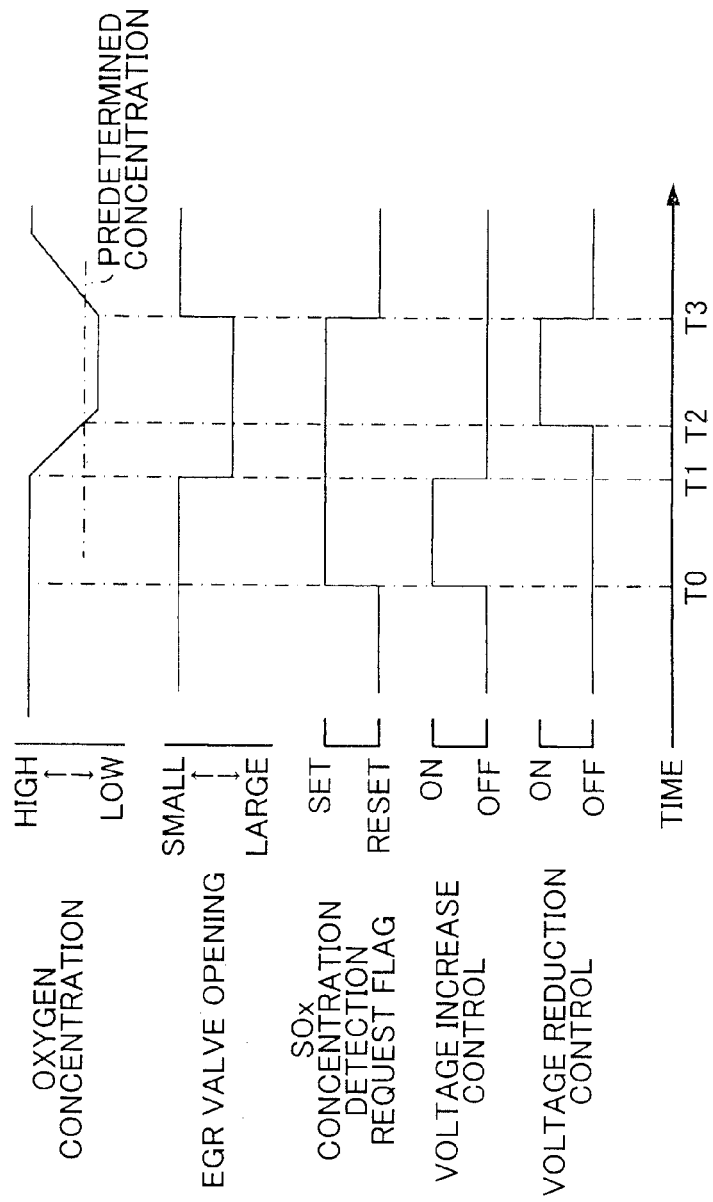
FIG. 17 is a time chart showing implementation of SOx concentration detection according to a fifth embodiment.

The SOx concentration detection according to the fifth embodiment will, now be described with reference to FIG. 17. In the example shown in FIG. 17, the oxygen concentration of the exhaust gas is higher than the predetermined concentration up to a time T0. When the SOx concentration detection request flag is set at the time T0, the voltage increase control is implemented. When the voltage increase control is completed at a time T1, the EGR valve opening is increased (in other words, the oxygen concentration control is implemented). As a result, the oxygen concentration of the exhaust gas gradually decreases. When the oxygen concentration of the exhaust gas falls to or below the predetermined concentration at a time T2, the voltage reduction control is implemented. When the voltage reduction control is completed at a time T3, the EGR valve opening is returned to normal (in other words, the oxygen concentration control is terminated). As a result, the oxygen concentration of the exhaust gas increases so as to rise above the predetermined concentration.

With the voltage increase control according to the fifth embodiment, the SOx concentration can be detected with a high degree of precision for identical reasons to the reasons described in relation to the first embodiment.

Figure 18:
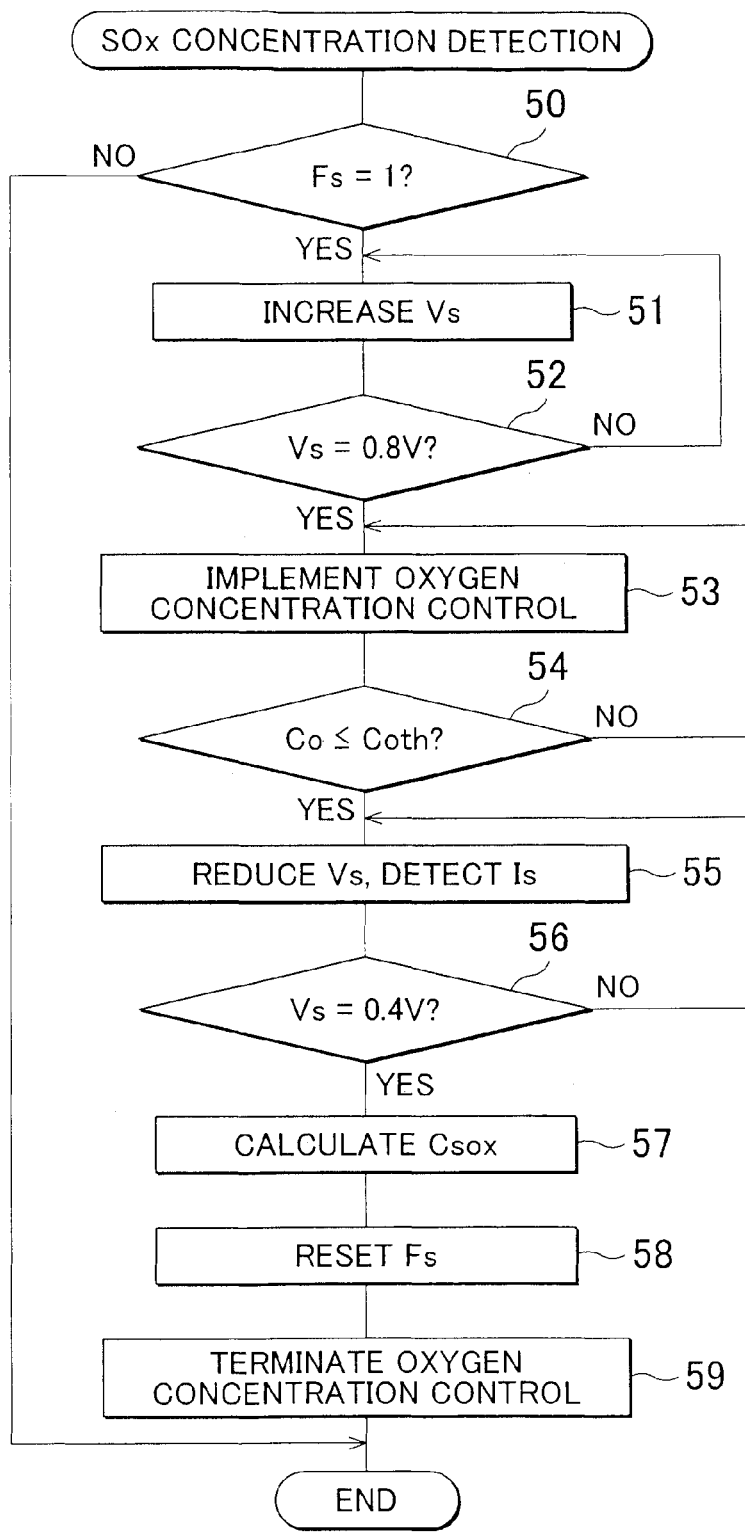
FIG. 18 shows an example of a SOx concentration detection flow according to the fifth embodiment.

An example of a flow of the SOx concentration detection according to the fifth embodiment will now be described with reference to FIG. 18. When the flow of FIG. 18 is started, the applied voltage is maintained at 0.4 V. Then, in step 50, a determination is made as to whether or not the SOx concentration detection request flag Fs is set (Fs=1). Here, when it is determined that Fs=1, the flow advances to step 51. When it is determined that Fs=1 is not established, on the other hand, the flow is terminated as is.

In step 51, the applied voltage Vs is increased from 0.4 V toward 0.8 V. Next, in step 52, a determination is made as to whether or not the applied voltage Vs has reached 0.8 V (Vs=0.8 V). Here, when it is determined that Vs=0.8 V, the flow advances to step 53. When it is determined that Vs=0.8 V is not established, on the other hand, the flow returns to step 51. Hence, the applied voltage Vs is increased continuously until it is determined in step 52 that Vs=0.8 V.

In step 53, the oxygen concentration control is implemented. The oxygen concentration control is control for controlling the oxygen concentration of the exhaust gas at or below the predetermined concentration. Next, in step 54, a determination is made as to whether or not the oxygen concentration Co of the exhaust gas is less than the predetermined concentration Coth (Co≤Coth). Here, when it is determined that Co≤Coth, the flow advances to step 55. When it is determined that Co≤Coth is not established, on the other hand, the flow returns to step 53. Hence, the oxygen concentration control is continued until it is determined in step 54 that Co≤Coth.

In step 55, the applied voltage Vs is reduced from 0.8 V toward 0.4 V, and the output current Is is detected. Next, in step 56, a determination is made as to whether or not the applied voltage Vs has reached 0.4 V (Vs=0.4 V). Here, when it is determined that Vs=0.4 V, the flow advances to step 57. When it is determined that Vs=0.4 V is not established, on the other hand, the flow returns to step 55. Hence, reduction of the applied voltage Vs and detection of the output current Is are continued until it is determined in step 56 that Vs=0.4 V.

In step 57, the SOx concentration Csox is calculated on the basis of the peak value of the output current Is detected in step 55. Next, in step 58, the SOx concentration detection request flag Fs is reset. Next, in step 59, the oxygen concentration control is terminated, whereupon the flow is terminated.

Next, SOx concentration detection according to a sixth embodiment will be described. In this SOx concentration detection, the voltage increase control is implemented when detection of the SOx concentration is requested. When the voltage increase control is complete, the voltage reduction control is implemented while implementing a low oxygen concentration operation. Here, the low oxygen concentration operation is the aforesaid operation of the internal combustion engine in which the oxygen concentration of the exhaust gas is held at or below a predetermined concentration.

Figure 19:
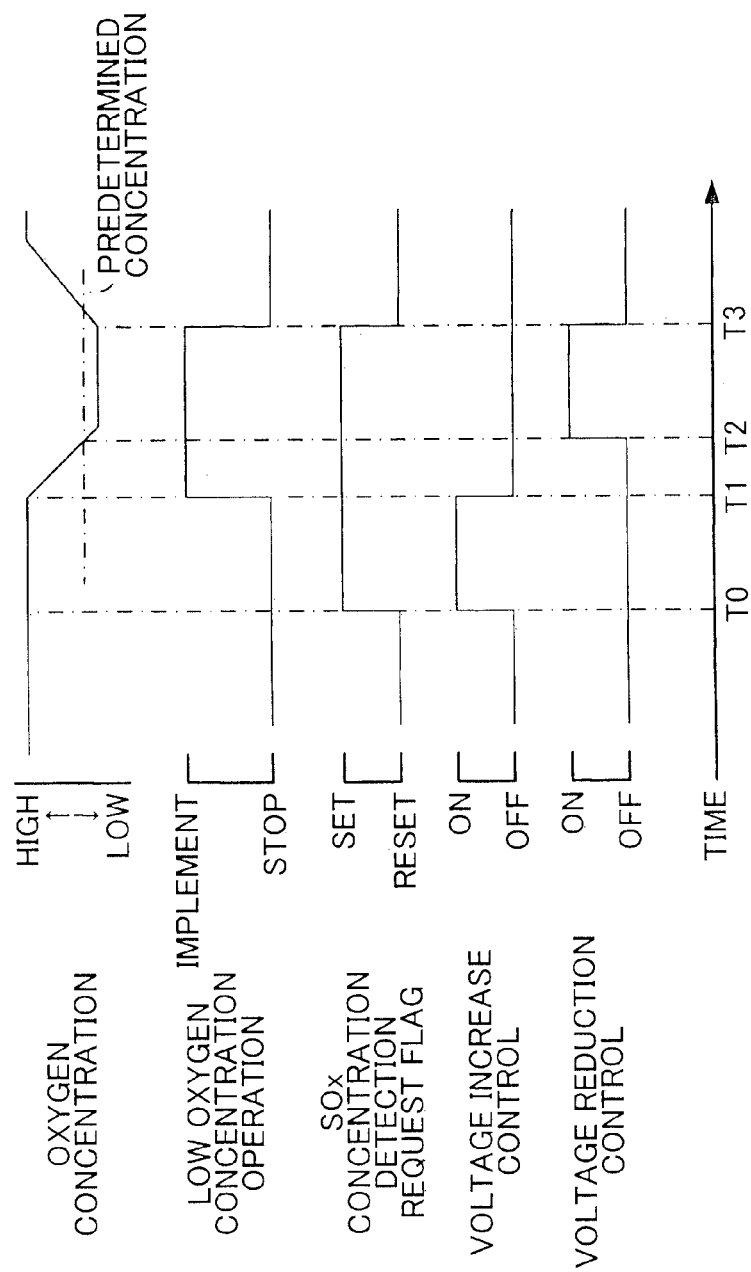
FIG. 19 is a time chart showing implementation of SOx concentration detection according to a sixth embodiment.

The SOx concentration detection according to the sixth embodiment will now be described with reference to FIG. 19. In the example shown in FIG. 19, the oxygen concentration of the exhaust gas is higher than the predetermined concentration up to a time T0. When the SOx concentration detection request flag is set at the time T0, the voltage increase control is implemented. When the voltage increase control is completed at a time T1, the low oxygen concentration operation is implemented. As a result, the oxygen concentration of the exhaust gas gradually decreases. When the oxygen concentration of the exhaust gas falls to or below the predetermined concentration at a time T2, the voltage reduction control is implemented. When the voltage reduction control is completed at a time T3, the low oxygen concentration operation is terminated. As a result, the oxygen concentration of the exhaust gas increases so as to rise above the predetermined concentration.

With the voltage increase control according to the sixth embodiment, the SOx concentration can be detected with a high degree of precision for identical reasons to the reasons described in relation to the first embodiment.

Figure 20:
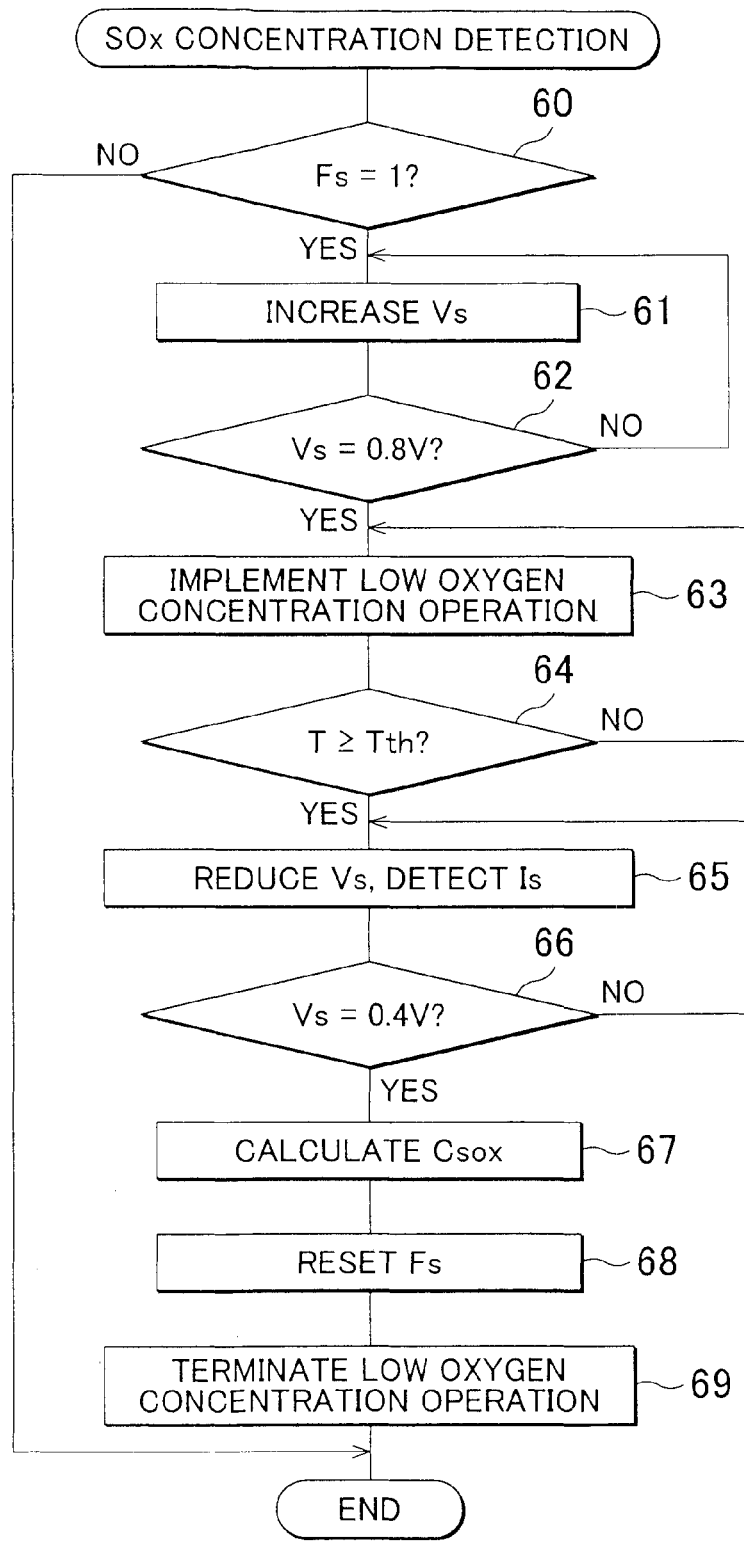
FIG. 20 shows an example of a SOx concentration detection flow according to the sixth embodiment.

An example of a flow of the SOx concentration detection according to the sixth embodiment will now be described with reference to FIG. 20. When the flow of FIG. 20 is started, the applied voltage is maintained at 0.4 V. Then, in step 60, a determination is made as to whether or not the SOx concentration detection request flag Fs is set (Fs=1). When it is determined that Fs=1, the flow advances to step 61. When it is determined that Fs=1 is not established, on the other hand, the flow is terminated as is.

In step 61, the applied voltage Vs is increased from 0.4 V toward 0.8 V. Next, in step 62, a determination is made as to whether or not the applied voltage Vs has reached 0.8 V (Vs=0.8 V). Here, when it is determined that Vs=0.8 V, the flow advances to step 63. When it is determined that Vs=0.8 V is not established, on the other hand, the flow returns to step 61. Hence, the applied voltage Vs is increased continuously until it is determined in step 62 that Vs=0.8 V.

In step 63, the low oxygen concentration operation is implemented. The low oxygen concentration operation is an operation of the internal combustion engine in which the oxygen concentration of the exhaust gas is held at or below the predetermined concentration. Next, in step 64, a determination is made as to whether or not the elapsed time T following the start of the low oxygen concentration operation in step 63 equals or exceeds the predetermined time Tth (T≥Tth). Here, when it is determined that T≥Tth, the flow advances to step 65. When it is determined that T≥Tth is not established, on the other hand, the flow returns to step 63. Hence, the low oxygen concentration operation is continued until it is determined in step 64 that T≥Tth.

In step 65, the applied voltage Vs is reduced from 0.8 V toward 0.4 V, and the output current Is is detected. Next, in step 66, a determination is made as to whether or not the applied voltage Vs has reached 0.4 V (Vs=0.4 V). Here, when it is determined that Vs=0.4 V, the flow advances to step 67. When it is determined that Vs=0.4 V is not established, on the other hand, the flow returns to step 65. Hence, reduction of the applied voltage Vs and detection of the output current Is are continued until it is determined in step 66 that Vs=0.4 V.

In step 67, the SOx concentration Csox is calculated on the basis of the peak value of the output current Is detected in step 65. Next, in step 68, the SOx concentration detection request flag Fs is reset. Next, in step 69, the low oxygen concentration operation is terminated, whereupon the flow is terminated.

Next, oxygen concentration control according to a seventh embodiment will be described. In the seventh embodiment; high sensor temperature control for controlling a sensor temperature to or above an oxygen concentration detection temperature is implemented. Here, in the SOx concentration detection according to the seventh embodiment, when detection of the SOx concentration is requested, or in other words when implementation of the voltage increase control is requested, the voltage increase control is implemented while performing oxygen concentration control and low sensor temperature control. More specifically, when detection of the SOx concentration is requested, the voltage increase control is implemented while implementing the oxygen concentration control and controlling an operation of the heater so that the sensor temperature is held at or below a predetermined upper limit temperature.

An S component of the exhaust gas adheres to the first sensor electrode during the voltage increase control. The predetermined upper limit temperature is a maximum temperature at which the S component does not separate from the first sensor electrode. Alternatively, the predetermined upper limit temperature is a maximum temperature at which an amount or a proportion of S component that separates from the first sensor electrode, from the S component of the exhaust gas that adheres to the first sensor electrode during the voltage increase control, is suppressed to a smaller value than a predetermined value. In particular, the predetermined upper limit temperature is a lower temperature than the oxygen concentration detection temperature. More specifically, the predetermined upper limit temperature is a lower temperature than 700° C.

Further, the oxygen concentration detection temperature is a sensor temperature required to output an output current that corresponds precisely to the oxygen concentration of the exhaust gas from the sensor when a sensor is used to detect the oxygen concentration of the exhaust gas. In other words, the oxygen concentration detection temperature is a suitable sensor temperature for detecting the oxygen concentration using a sensor. More specifically, the oxygen concentration detection temperature is a temperature within a range of 700° C. to 800° C., for example.

Figure 21:
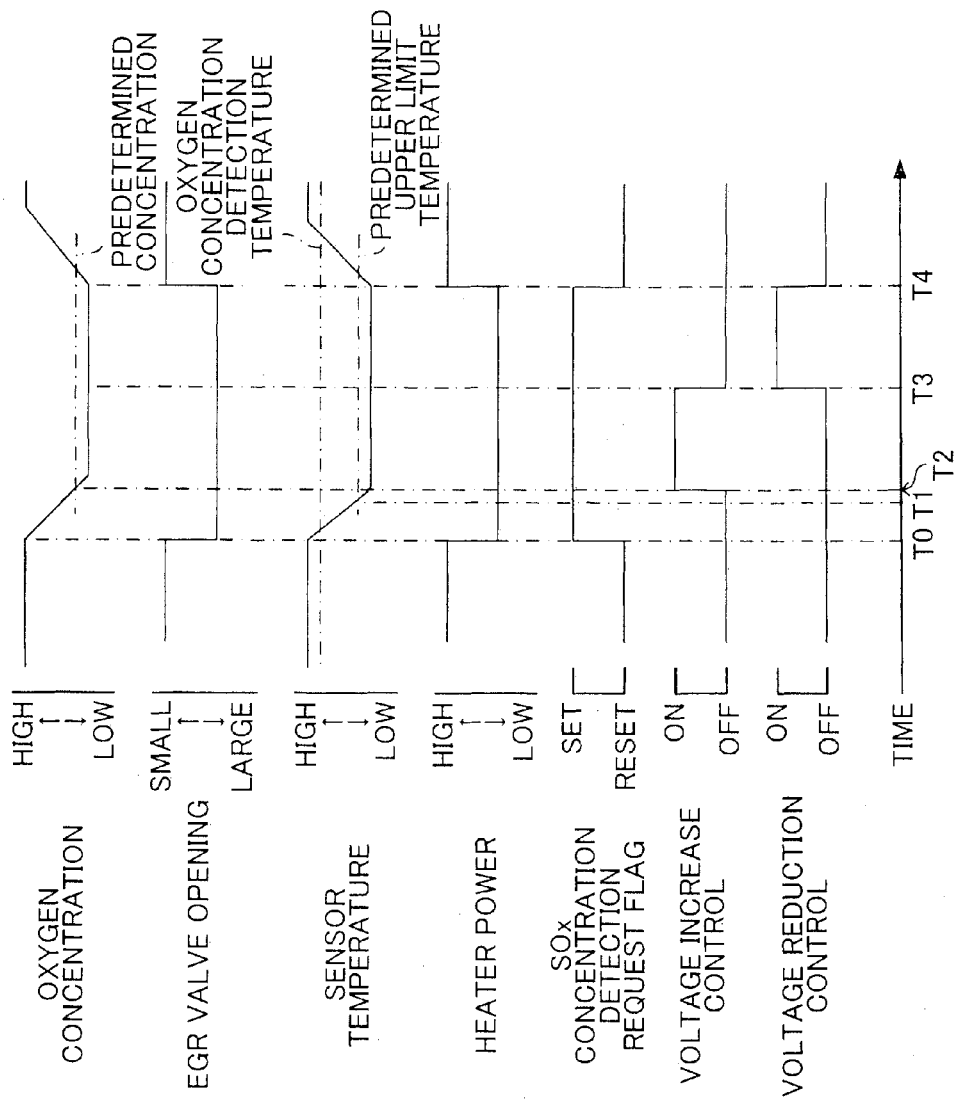
FIG. 21 is a time chart showing implementation of SOx concentration detection according to a seventh embodiment.

The SOx concentration detection according to the seventh embodiment will now be described with reference to FIG. 21. In the example shown in FIG. 21, up to a time T0, the oxygen concentration of the exhaust gas is higher than a predetermined concentration, and the sensor temperature is controlled to or above the oxygen concentration detection temperature by implementing the high sensor temperature control. When the SOx concentration detection request flag is set at the time T0, the EGR valve opening is increased, and a heater power is reduced by implementing the low sensor temperature control. As a result, the oxygen concentration of the exhaust gas gradually decreases, and the sensor temperature gradually decreases. The sensor temperature falls to or below the predetermined upper limit temperature at a time T1, and the oxygen concentration of the exhaust gas falls to or below the predetermined concentration at a time T2. Accordingly, the voltage increase control is implemented. The voltage increase control is completed at a time T3, and simultaneously, the voltage reduction control is implemented. When the voltage reduction control is completed at a time T4, the EGR valve opening is returned to normal (in other words, the oxygen concentration control is terminated), and the heater power is increased so as to return to normal by terminating the low sensor temperature control and implementing the high sensor temperature control. As a result, the oxygen concentration of the exhaust gas increases so as to exceed the predetermined concentration, and the sensor temperature increases so as to equal or exceed the oxygen concentration detection temperature.

With the SOx concentration detection according to the seventh embodiment, the SOx concentration can be detected with a high degree of precision for identical reasons to the reasons described in relation to the first embodiment. Additionally, the SOx concentration can be calculated with a high degree of precision for the following reason.

When the applied voltage is increased from 0.4 V to 0.8 V, SOx is broken down on the first sensor electrode due to the increase in the applied voltage such that the S component (i.e. a sulfur component) of the SOx adheres (or adsorbs) to the first sensor electrode. Here, when the sensor temperature during the voltage increase control is high, the sulfur component adhered to the first sensor electrode may separate from the first sensor electrode. When the sulfur component separates from the first sensor electrode, the output current obtained from the sensor during the voltage reduction control (i.e. the control for reducing the applied voltage from 0.8 V to 0.4 V) implemented after the voltage increase control does not correspond accurately to the SOx concentration.

When the sensor temperature during the voltage increase control is low, on the other hand, the sulfur component that adheres to the first sensor electrode during the voltage increase control does not separate from the first sensor electrode (or at least separation from the first sensor electrode of the sulfur component adhered to the first sensor electrode is suppressed), and as a result, the output current obtained from the sensor during the voltage reduction control implemented after the voltage increase control corresponds accurately to the SOx concentration. With the SOx concentration detection according to the seventh embodiment, therefore, the SOx concentration can be calculated with a high degree of precision.

In consideration of the advantages of the SOx concentration detection according to the seventh embodiment, described above, it may be said that SOx is a component in which the S component of the SOx adheres to the sensor (in particular, the first sensor electrode) during the voltage increase control, and when the sensor temperature during the voltage increase control is low, the S component adhered to the sensor does not separate from the sensor (or at least separation from the sensor of the S component adhered to the sensor is suppressed).

The concept of the SOx concentration detection according to the seventh embodiment may also be applied to calculation of a SOx related parameter according to which the SOx in the exhaust gas adheres to the sensor during the voltage increase control and does not separate from the sensor (or at least separation thereof from the sensor is suppressed) when the sensor temperature during the voltage increase control is low.

In the low sensor temperature control according to the seventh embodiment, control may be performed to set the sensor temperature at or above a predetermined lower limit temperature. In other words, the sensor temperature during the voltage increase control may be controlled to a predetermined temperature range (i.e. a temperature range between the predetermined upper limit temperature and the predetermined lower limit temperature).

In this case, the SOx concentration can be detected with a high degree of precision. More specifically, when the sensor temperature during the voltage increase control is too low, adhesion of the S component to the sensor during the voltage increase control may not progress. Hence, by implementing the voltage increase control while controlling the sensor temperature to the temperature range between the predetermined upper limit temperature and the predetermined lower limit temperature, adhesion of the S component to the sensor during the voltage increase control progresses sufficiently. As a result, the SOx concentration can be detected with a high degree of precision.

In consideration of this advantage relating to the predetermined lower limit temperature, it may be said that the predetermined lower limit temperature is a sensor temperature at which adhesion of the S component to the sensor during the voltage increase control progresses sufficiently. More specifically, the predetermined lower limit temperature equals or exceeds 500° C.

Figure 22:
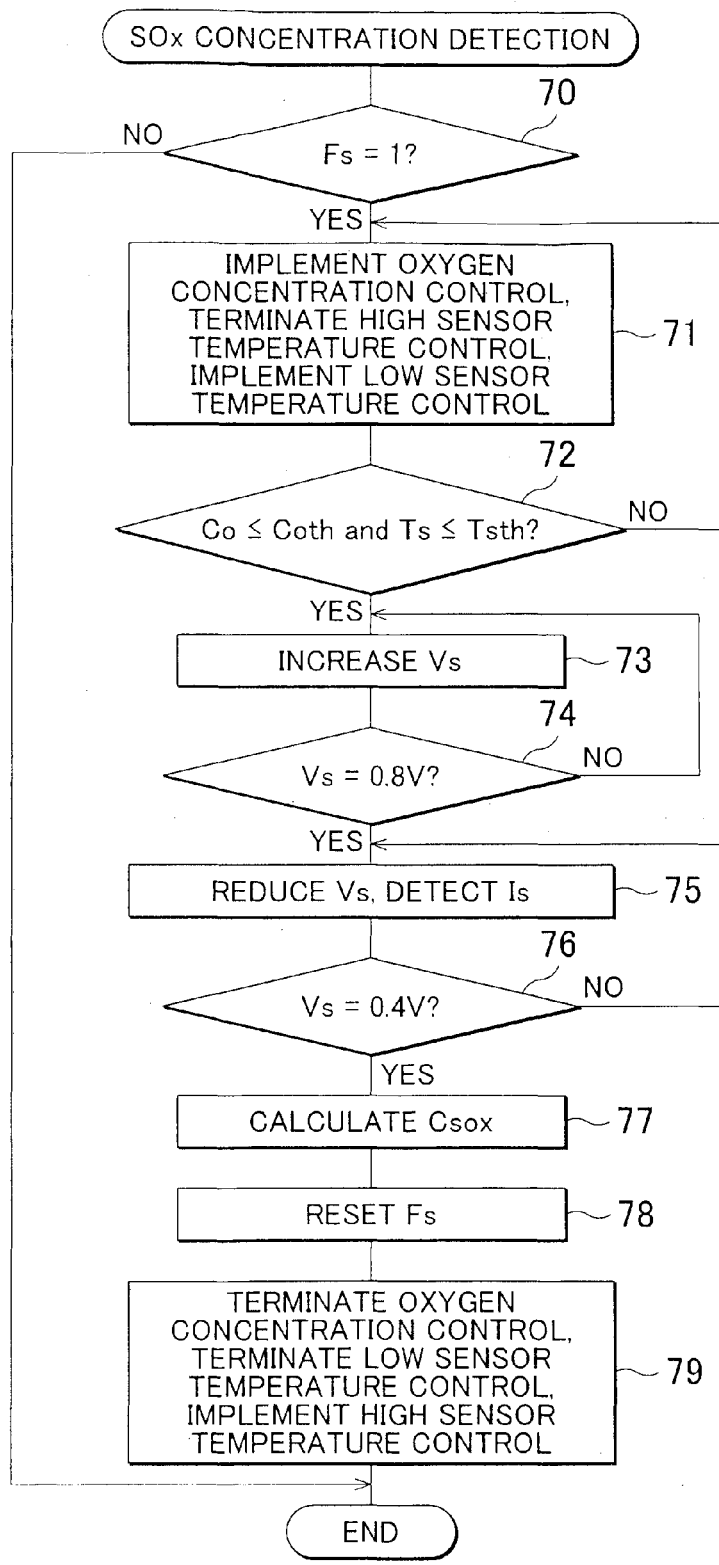
FIG. 22 shows an example of a SOx concentration detection flow according to the seventh embodiment.

An example of a flow of the SOx concentration detection according to the seventh embodiment will now be described with reference to FIG. 22. When the flow of FIG. 22 is started, the applied voltage is maintained at 0.4 V. Then, in step 70, a determination is made as to whether or not the SOx concentration detection request flag Fs is set (Fs=1). Here, when it is determined that Fs=1, the flow advances to step 71. When it is determined that Fs=1 is not established, on the other hand, the flow is terminated as is.

In step 71, the oxygen concentration control is implemented, the high sensor temperature control is terminated, and the low sensor temperature control is implemented. Next, in step 72, a determination is made as to whether or not the oxygen concentration Co of the exhaust gas is less than the predetermined concentration Coth and a sensor temperature Ts is less than a predetermined upper limit temperature Tsuth (Co≤Coth and Ts≤Tsuth). Here, when it is determined that Co≤Coth and Ts≤Tsuth, the flow advances to step 73. When it is determined that Co≤Coth and Ts≤Tsuth are not established, on the other hand, the flow returns to step 71. Hence, the oxygen concentration control and the low sensor temperature control are continued until it is determined in step 72 that Co≤Coth and Ts≤Tsuth.

In step 73, the applied voltage Vs is increased from 0.4 V toward 0.8 V. Next, in step 74, a determination is made as to whether or not the applied voltage Vs has reached 0.8 V (Vs=0.8 V). Here, when it is determined that Vs=0.8 V, the flow advances to step 75. When it is determined that Vs=0.8 V is not established, on the other hand, the flow returns to step 73. Hence, the applied voltage Vs is increased continuously until it is determined in step 74 that Vs=0.8 V.

In step 75, the applied voltage Vs is reduced from 0.8 V toward 0.4 V, and the output current Is is detected. Next, in step 76, a determination is made as to whether or not the applied voltage Vs has reached 0.4 V (Vs=0.4 V). Here, when it is determined that Vs=0.4 V, the flow advances to step 77. When it is determined that Vs=0.4 V is not established, on the other hand, the flow returns to step 75. Hence, reduction of the applied voltage Vs and detection of the output current Is are continued until it is determined in step 76 that Vs=0.4 V.

In step 77, the SOx concentration Csox is calculated on the basis of the peak value of the output current Is detected in step 75. Next, in step 78, the SOx concentration detection request flag Fs is reset. Next, in step 79, the oxygen concentration control is terminated, the low sensor temperature control is terminated, and the high sensor temperature control is implemented, whereupon the flow is terminated.

Next, SOx concentration detection according to an eighth embodiment will be described. In the eighth embodiment, the SOx concentration detection according to the first to seventh embodiments described above is implemented a predetermined number of times, and the SOx concentration detected during the SOx concentration detection in which the oxygen concentration of the exhaust gas during the voltage reduction control was lowest, among the implemented SOx concentration detections, is employed as the SOx concentration of the exhaust gas.

As described above, the output current obtained during the voltage reduction control corresponds to the SOx concentration steadily more accurately as the oxygen concentration of the exhaust gas decreases. By employing the SOx concentration detected when the oxygen concentration of the exhaust gas is lowest as the SOx concentration of the exhaust gas, therefore, the SOx concentration can be detected with an even higher degree of precision. This concept is particularly useful in a case where the oxygen concentration of the exhaust gas during the voltage reduction control differs in each implementation of the voltage reduction control (in particular, a case in which the voltage increase control or the voltage reduction control is implemented when the oxygen concentration of the exhaust gas falls to or below a predetermined concentration, rather than actively controlling the oxygen concentration of the exhaust gas at or below the predetermined concentration).

Next, a ninth embodiment will be described. In the ninth embodiment, the applied voltage is kept steady at 0.4 V. During SOx concentration detection according to the ninth embodiment, the voltage increase control is implemented when the oxygen concentration of the exhaust gas is less than a predetermined concentration, or when a low oxygen concentration condition according to which the oxygen concentration of the exhaust gas is predicted to be less than the predetermined concentration is established, whereupon the voltage reduction control is implemented. At this time, the ECU determines whether or not an absolute value of the peak value of the output current input into the ECU during the voltage reduction control equals or exceeds a warning determination value. When the absolute value of the peak value equals or exceeds the warning determination value, the ECU issues a warning indicating an abnormality in a fuel property. In this case, it may be said that a parameter for determining the need to issue a warning indicating an abnormality in the fuel property is calculated as the SOx related parameter. When the absolute value of the peak value is smaller than the warning determination value, on the other hand, the ECU calculates (detects) the SOx concentration using the peak value and the reference current.

The warning determination value according to the ninth embodiment is set as follows, for example. As described above, the sulfur component of the SOx in the exhaust gas may adhere to the first sensor electrode, and the inventors of this application discovered through research that as an S adhesion amount increases, the absolute value of the peak value increases. When the S adhesion amount is extremely large, the detection precision of the limiting current sensor, in particular the precision with which the SOx concentration is detected, may decrease. One of the causes of an increase in the S adhesion amount is a high SOx concentration in the exhaust gas. When a sulfur component concentration of fuel is high, the SOx concentration of the exhaust gas increases. Hence, when the sulfur component concentration of the fuel exceeds an allowable concentration, leading to the possibility of an abnormality in the fuel property, a corresponding warning is preferably issued.

The warning determination value according to the ninth embodiment is set, for example, at an appropriately selected value that equals or exceeds a minimum value of the absolute value of the peak value (in other words, the absolute value of the peak value of the output current input into the ECU during the voltage reduction control) when the fuel property is not within an allowable range, and more particularly when the S concentration of the fuel is higher than the allowable concentration.

With the SOx concentration detection according to the ninth embodiment, a warning is issued when the possibility of an abnormality in the fuel property exists, and therefore notification can be provided of the possibility of an abnormality in the fuel property.

An example of a flow of the SOx concentration detection according to the ninth embodiment will now be described with reference to FIG. 23. Steps 80 to 86 in the flow of FIG. 23 are identical to steps 10 to 16 in the flow of FIG. 10, and therefore description of these steps has been omitted.

Figure 23:
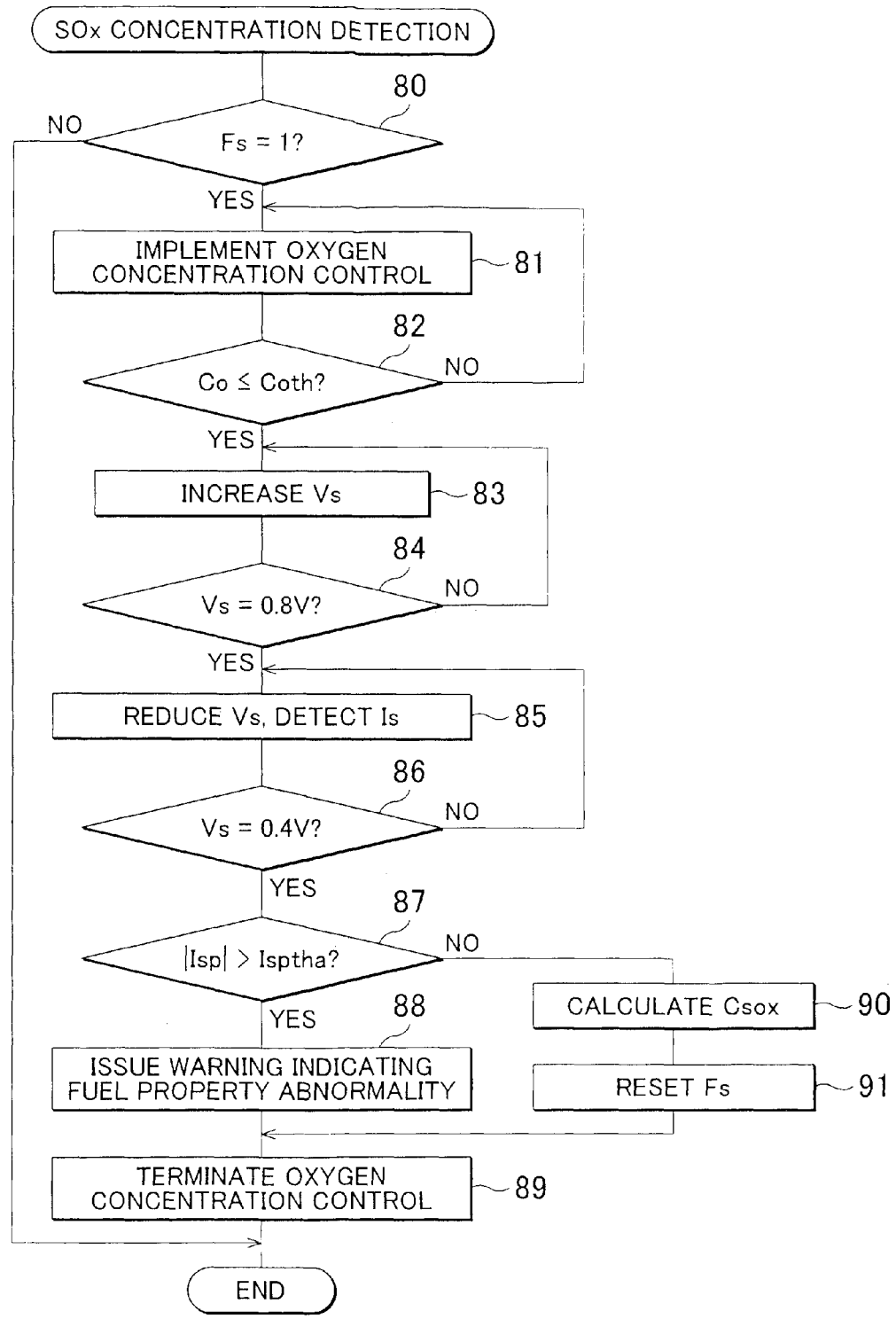
FIG. 23 shows an example of a SOx concentration detection flow according to the ninth embodiment.

In step 87 of the flow in FIG. 23, a determination is made as to whether or not an absolute value |Isp| of the peak value of the output current Is detected in step 85 is larger than a warning determination value Isptha (|Isp|>Isptha). When it is determined that |Isp|>Isptha, the flow advances to step 88, where a warning indicating a fuel property abnormality is issued, whereupon the flow advances to step 89. When it is determined that |Isp|>Isptha is not established, on the other hand, the flow advances to step 90, where the SOx concentration Csox is calculated on the basis of the peak value of the output current Is detected in step 85. Next, in step 91, the SOx concentration detection request flag Fs is reset, whereupon the flow advances to step 89.

In step 89, heater power control I is terminated and the oxygen concentration control is terminated, whereupon the flow is terminated.

Next, a tenth embodiment will be described. In the tenth embodiment, similarly to the ninth embodiment, the voltage increase control is implemented, followed by the voltage reduction control. At this time, the ECU determines whether or not the absolute value of the peak value of the output current input into the ECU during the voltage reduction control equals or exceeds a determination value for implementing sulfur poisoning recovery control. When the absolute value of the peak value equals or exceeds the determination value, the ECU implements the sulfur poisoning recovery control. In this case, it may be said that a parameter for determining the need to implement the sulfur poisoning recovery control is calculated as the SOx related parameter. When the absolute value of the peak value is smaller than the determination value, on the other hand, the ECU calculates (detects) the SOx concentration using the peak value and the reference current.

The determination value for implementing the sulfur poisoning recovery control according to the tenth embodiment is set as follows, for example. The sulfur component of the SOx in the exhaust gas may adhere to the first sensor electrode. The inventors of this application discovered through research that as the sulfur adhesion amount (i.e. the amount of sulfur adhered to the first sensor electrode) increases, the absolute value of the peak value increases. When the sulfur adhesion amount is extremely large, the detection precision of the limiting current sensor, in particular the precision with which the SOx concentration is detected, may decrease. Hence, when the sulfur adhesion amount is large, the sulfur adhered to the first sensor electrode is preferably removed, or in other words the sulfur poisoning recovery control is preferably implemented. The determination value for implementing the sulfur poisoning recovery control according to the tenth embodiment is set, for example, at the absolute value of the peak value, or in other words the absolute value of the peak value of the output current input into the ECU during the voltage reduction control, in a case where implementation of the sulfur poisoning recovery control is deemed necessary.

The determination value for implementing the sulfur poisoning recovery control according to the tenth embodiment may be identical or different to the warning determination value according to the ninth embodiment.

With the SOx concentration detection according to the tenth embodiment, when the possibility of a reduction in the detection precision of the sensor exists due to sulfur poisoning, the sulfur poisoning recovery control is implemented. In other words, the SOx concentration detection is implemented only when there is no possibility of a reduction in the detection precision of the sensor due to sulfur poisoning. Hence, with the SOx concentration detection according to the tenth embodiment, the SOx concentration can be detected with an even higher degree of precision.

The sulfur poisoning recovery control will now be described. This control is control for eliminating sulfur poisoning from the sensor 30. Sulfur poisoning is deterioration of the sensor 30, or more specifically the first sensor electrode 35A, caused by the SOx in the exhaust gas.

In this embodiment, the applied voltage is kept steady at 0.4 V. In other words, 0.4 V is applied steadily to the sensor. When sulfur poisoning recovery is requested, the applied voltage is increased from 0.4 V to 0.8 V and then reduced from 0.8 V to 0.4 V. In so doing, the sulfur poisoning of the sensor is reduced, and by repeating the control, the sulfur poisoning of the sensor is eventually eliminated.

An example of a flow of the SOx concentration detection according to the tenth embodiment will now be described with reference to FIG. 24. Steps 100 to 106 in the flow of FIG. 24 are identical to steps 10 to 16 in the flow of FIG. 10, and therefore description of these steps has been omitted.

Figure 24:
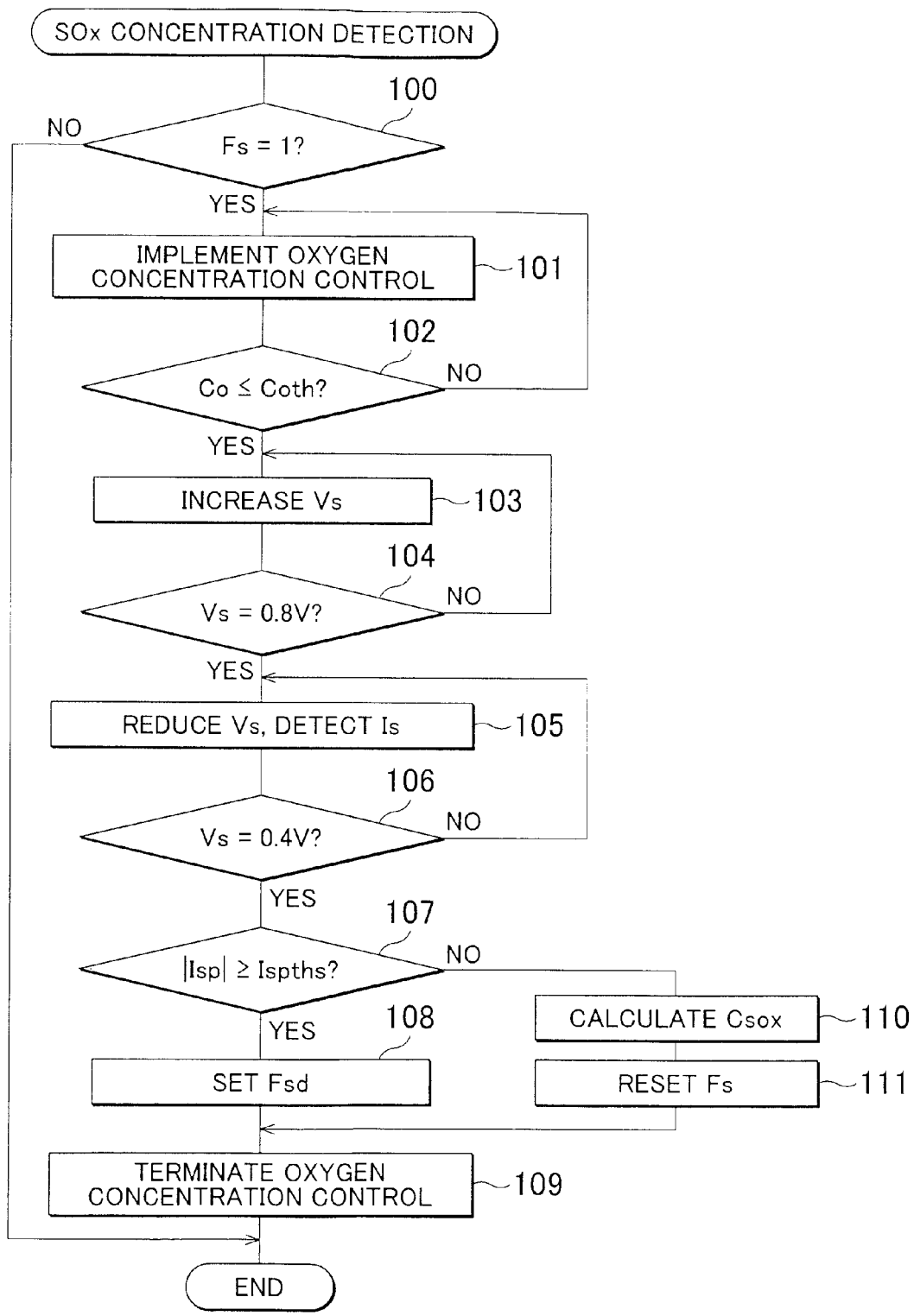
FIG. 24 shows an example of a SOx concentration detection flow according to the tenth embodiment.

In step 107 of the flow in FIG. 24, a determination is made as to whether or not the absolute value |Isp| of the peak value of the output current Is detected in step 105 equals or exceeds an S poisoning recovery implementation determination value Ispths (|Isp|≥Ispths). When it is determined that |Isp|≥Ispths, the flow advances to step 108, where a sulfur poisoning recovery request flag Fsd is set, whereupon the flow advances to step 109. In this case, the sulfur poisoning recovery request flag Fsd is set, and therefore the S poisoning recovery control is implemented. When it is determined that |Isp|≥Ispths is not established, on the other hand, the flow advances to step 110, where the SOx concentration Csox is calculated on the basis of the peak value of the output current Is detected in step 105. Next, in step 111, the SOx concentration detection request flag is reset, whereupon the flow advances to step 109.

In step 109, the oxygen concentration control is terminated, whereupon the flow is terminated.

Next, an eleventh embodiment will be described. In the eleventh embodiment, the applied voltage is kept steady at 0.4 V. In other words, 0.4 V is applied steadily to the sensor cell. Here, the 0.4 V voltage is a voltage that equals or exceeds the voltage Vth shown in FIG. 2, and a voltage at which the sensor cell output current remains constant irrespective of the sensor cell applied voltage when the air-fuel ratio of the exhaust gas is constant.

During SOx concentration/air-fuel ratio detection according to the eleventh embodiment, the ECU calculates (detects) the air-fuel ratio from the relationship shown in FIG. 2 on the basis of the sensor cell output current obtained when 0.4 V is applied steadily to the sensor cell.

Following a request for SOx concentration detection, on the other hand, the voltage increase control is implemented when the oxygen concentration of the exhaust gas is less than a predetermined concentration, or when the low oxygen concentration condition according to which the oxygen concentration of the exhaust gas is predicted to be less than the predetermined concentration is established, whereupon the voltage reduction control is implemented. At this time, the ECU calculates (detects) the SOx concentration using the peak value of the output current input into the ECU during the voltage reduction control, and the reference current.

The ECU calculates (detects) the air-fuel ratio from the relationship shown in FIG. 2 on the basis of the sensor cell output current even after the sensor cell applied voltage has been reduced from 0.8 V to 0.4 V. At this time, the sensor cell applied voltage is maintained at 0.4 V.

According to the eleventh embodiment, the air-fuel ratio of the exhaust gas and the SOx concentration of the exhaust gas can both be detected using a single sensor.

An example of a flow of the SOx concentration/air-fuel ratio detection according to the eleventh embodiment will now be described with reference to FIG. 25. Steps 121 to 129 in the flow of FIG. 25 are identical to steps 11 to 19 in the flow of FIG. 10, and therefore description of these steps has been omitted.

Figure 25:
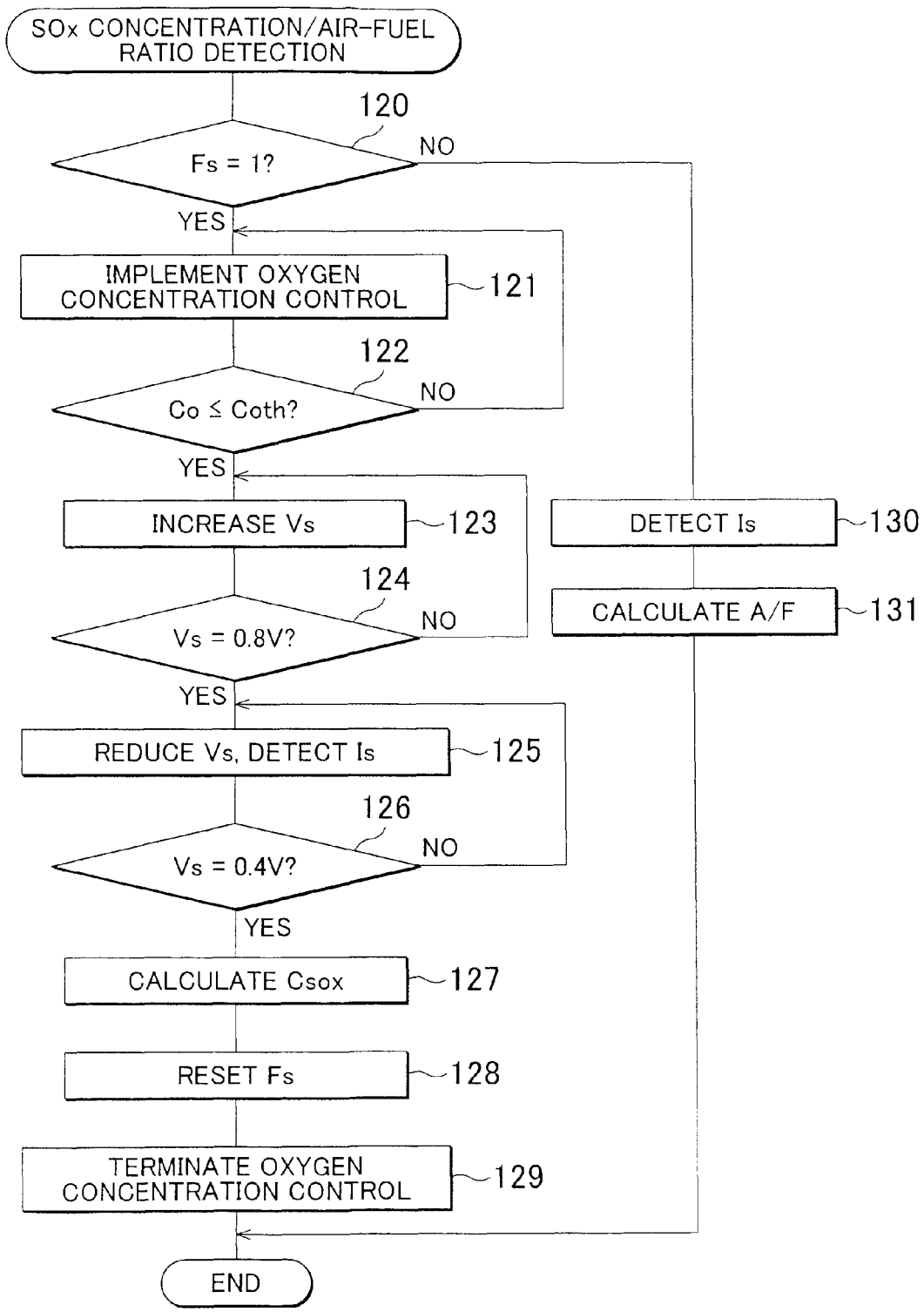
FIG. 25 shows an example of a SOx concentration/air-fuel ratio detection flow according to the eleventh embodiment.

When the flow of FIG. 25 is started, the applied voltage is maintained at 0.4 V. Then, in step 120, a determination is made as to whether or not the SOx concentration detection request flag Fs is set (Fs=1). When it is determined in step 120 that Fs=1, the flow advances to step 121. When it is determined that Fs=1 is not established, on the other hand, the flow advances to step 130.

In step 130, the output current Is is detected. Next, in step 131, an air-fuel ratio A/F is calculated on the basis of the output current Is detected in step 130. The flow is then terminated.

When the oxygen concentration of the exhaust gas is extremely low, for example equal to or smaller than 1%, the single cell type limiting current sensor described above can also be used to detect a NOx concentration of the exhaust gas. In this case, a voltage is applied to the sensor cell to break down the NOx in the exhaust gas such that a current is caused to flow to the sensor cell by oxygen in the NOx. The NOx concentration of the exhaust gas can be detected on the basis of the output current of the sensor, or more specifically the output current of the sensor cell, at this time.

According to the embodiments described above, when SOx concentration detection is requested in a case where the sensor described above is used as a sensor for detecting the oxygen concentration of the exhaust gas, it is possible to determine whether or not the oxygen concentration is less than the predetermined concentration using the oxygen concentration detected by the sensor before implementing the voltage increase control. Alternatively, a separate sensor capable of detecting the oxygen concentration may be provided in the exhaust passage upstream of the sensor, and the determination, as to whether or not the oxygen concentration is less than the predetermined concentration may be made using an oxygen concentration detected by this sensor.

When the internal combustion engine includes the limiting current sensor of FIG. 1, a circuit shown in FIG. 26, for example, is employed as a SOx detection circuit. The limiting current sensor 30 shown in FIG. 26 (or the limiting current sensor of FIG. 1) includes the heater 34 and the sensor cell 35. The limiting current sensor 30 is connected to the ECU 90, which includes an applied voltage command unit 91, a parameter calculation unit 92, and a heater control unit 93, an applied voltage control circuit 94, and an output current detection circuit 95.

In FIG. 26, the applied voltage command unit 91, the parameter calculation unit 92, and the heater control unit 93 represent constituent elements or functional blocks of the ECU 90.

The applied voltage command unit 91 transmits a command relating to the voltage to be applied to the sensor cell 35 to the applied voltage control circuit 94.

The parameter calculation unit 92 receives a signal corresponding to the sensor cell output current from the output current detection circuit 95, calculates the sensor cell output current on the basis of the received signal, and calculates the air-fuel ratio of the exhaust gas (or the oxygen concentration of the exhaust gas) or the SOx concentration of the exhaust gas on the basis of the calculated output current. The parameter calculation unit 92 calculates a circuit impedance of the sensor 30 on the basis of a signal received from the output current detection circuit 95, and transmits information relating to the calculated impedance to the heater control unit 93. The heater control unit 93 transmits a control signal for controlling the heater 34 to the heater 34 on the basis of the information relating to the impedance received from the parameter calculation unit 92.

The applied voltage control circuit 94 controls the sensor cell applied voltage on the basis of the command received from the applied voltage command unit 91. Alternatively, the applied voltage control circuit 94 controls the sensor cell applied voltage on the basis of the command received from the applied voltage command unit 91 and a signal corresponding to the sensor cell output current, provided by the output current detection circuit 95.

The output current detection circuit 95 detects the sensor cell output current, and transmits a signal corresponding to the detected output current to the parameter calculation unit 92 and the applied voltage control circuit 94.

In the SOx concentration detection according to the above embodiments, the reason why the current corresponding to the SOx concentration is output from the sensor during reduction of the applied voltage is that a SOx related reaction is assumed to be underway in the sensor cell. The reaction is greatly affected by the temperature of the sensor cell, and therefore, in consideration of the extremely low SOx concentration of the exhaust gas, the temperature of the sensor cell is preferably kept constant. Hence, during implementation of the SOx concentration detection according to the above embodiments, the heater may be controlled such that the temperature of the sensor cell is kept constant. Thus, the SOx concentration is detected with an even higher degree of precision.

The SOx concentration detection according to the above embodiments is particularly preferably implemented immediately after, or as soon as possible after, refueling (in other words, replenishment of a fuel tank with fuel to be supplied to the fuel injection valve).

The above embodiments are embodiments of a case in which the SOx concentration of the exhaust gas is detected. However, the concept of the above embodiments may be applied widely to cases in which a SOx related parameter (for example, a coefficient that is used to control an internal combustion engine and set in accordance with an amount of SOx) having a correlation with an output current obtained when an applied voltage is reduced from a predetermined voltage is calculated. In such cases, it must be possible to differentiate the output current that correlates with the SOx related parameter to be detected from output currents correlating with other SOx related parameters.

To put it another way, the concept of the above embodiments may also be applied to a case in which a SOx related parameter that either does not correlate with (or has an extremely small correlation with) an output current obtained when the applied voltage is maintained at a constant voltage, or does not correlate (or slightly correlates) with an output current obtained when the applied voltage is increased but does correlate with an output current obtained when the applied voltage is reduced from a predetermined voltage, is calculated.

The above embodiments are embodiments of a case in which the SOx concentration is detected using the minimum value of the output current during the voltage reduction control. The concept of the above embodiments may also be applied to a case in which the SOx related parameter is calculated using a maximum value of the output current during the voltage reduction control.

The concept of the above embodiments may also be applied to a two-cell type limiting current sensor. A two-cell type limiting current sensor is a sensor in which a pump cell that discharges the oxygen in the exhaust gas is provided in the sensor upstream of the sensor cell.

The invention was described above with references to embodiments thereof, but the invention is not limited to the embodiments and structures described above, and various amendments and equivalent configurations may be applied to the invention. Further, as regards the various constituent elements of the embodiments, more limited configurations and various combinations of the configurations are also included in the scope of the invention.

What is claimed is:

1. A control apparatus for an internal combustion engine having a limiting current sensor, the control apparatus comprising:
an electronic control unit configured to:
(i) calculate a parameter relating to SOx contained in a detection subject gas using an output current of the sensor, the output current being obtained when voltage reduction control is implemented to reduce an applied voltage applied to the sensor from a parameter calculation voltage; and
(ii) implement the voltage reduction control when an oxygen concentration of the detection subject gas is less than a predetermined concentration.

2. The control apparatus according to claim 1, wherein the electronic control unit is configured to warn that a fuel property is abnormal when an absolute value of the output current during the voltage reduction control equals or exceeds a warning determination value.

3. The control apparatus according to claim 1, wherein the electronic control unit is configured to implement voltage increase control to increase the applied voltage, that is applied to the sensor, to the parameter calculation voltage before implementing the voltage reduction control and when a temperature of the sensor is less than a predetermined upper limit temperature.

4. The control apparatus according to claim 1, wherein the electronic control unit is configured to employ a parameter calculated when the oxygen concentration of the detection subject gas is lowest, from among a plurality of calculated parameters, as a final parameter relating to SOx.

5. The control apparatus according to claim 1, wherein the electronic control unit is configured to implement control to eliminate sulfur poisoning from the sensor when the output current during the voltage reduction control equals or exceeds a determination value.

6. The control apparatus according to claim 1, wherein the parameter calculation voltage is a voltage that is equal to or higher than 0.8 V.

7. The control apparatus according to claim 1, wherein the applied voltage upon completion of the voltage reduction control is less than 0.7 V.

8. The control apparatus according to claim 1, wherein the electronic control unit is configured to apply a first voltage that is lower than the parameter calculation voltage steadily to the sensor, and detect the oxygen concentration of the detection subject gas using the output current of the sensor obtained when the first voltage is applied to the sensor.

9. The control apparatus according to claim 1, wherein the electronic control unit is configured to implement the voltage reduction control after controlling the oxygen concentration of the detection subject gas at or below the predetermined concentration.

10. The control apparatus according to claim 9, wherein the electronic control unit is configured to implement voltage increase control to increase the applied voltage applied to the sensor to the parameter calculation voltage before implementing the voltage reduction control, and control the oxygen concentration of the detection subject gas at or below the predetermined concentration only during implementation of the voltage reduction control.

11. A control apparatus for an internal combustion engine having a limiting current sensor, the control apparatus comprising:
an electronic control unit configured to:
(iii) calculate a parameter relating to SOx contained in a detection subject gas using an output current of the sensor, the output current being obtained when voltage reduction control is implemented to reduce an applied voltage applied to the sensor from a parameter calculation voltage; and
(iv) implement the voltage reduction control when a low oxygen concentration condition, according to which an oxygen concentration of the detection subject gas is predicted to be less than a predetermined concentration, is established.

12. The control apparatus according to claim 11, wherein the electronic control unit is configured to implement the voltage reduction control after establishing the low oxygen concentration condition.

13. The control apparatus according to claim 12, wherein the electronic control unit is configured to implement voltage increase control to increase the applied voltage applied to the sensor to the parameter calculation voltage before implementing the voltage reduction control, and establish the low oxygen concentration condition only during implementation of the voltage reduction control.

14. A control method for an internal combustion engine having a limiting current sensor, the control method comprising:
calculating a parameter relating to SOx contained in a detection subject gas using an output current of the sensor, the output current being obtained when voltage reduction control is implemented to reduce an applied voltage applied to the sensor from a parameter calculation voltage; and
implementing the voltage reduction control when an oxygen concentration of the detection subject gas is less than a predetermined concentration.

15. A control method for an internal combustion engine having a limiting current sensor, the control method comprising:
calculating a parameter relating to SOx contained in a detection subject gas using an output current of the sensor, the output current being obtained when voltage reduction control is implemented to reduce an applied voltage applied to the sensor from a parameter calculation voltage; and
implementing the voltage reduction control when a low oxygen concentration condition, according to which an oxygen concentration of the detection subject gas is predicted to be less than a predetermined concentration, is established.

* * * * *